US006376182B1

(12) United States Patent
Chao et al.

(10) Patent No.: US 6,376,182 B1
(45) Date of Patent: Apr. 23, 2002

(54) METHODS AND COMPOSITIONS FOR CORRELATING TISSUE KALLIKREIN GENE PROMOTER POLYMORPHISMS WITH TREATMENT OF ESSENTIAL HYPERTENSION

(75) Inventors: Lee Chao; Julie Chao, both of Mt. Pleasant; Qing Song, Charleston, all of SC (US)

(73) Assignee: Medical University of South Carolina, Charleston, SC (US)

( * ) Notice: Subject to any disclaimer, the term of this patent is extended or adjusted under 35 U.S.C. 154(b) by 0 days.

(21) Appl. No.: 09/495,140

(22) Filed: Jan. 31, 2000

Related U.S. Application Data

(63) Continuation-in-part of application No. 09/389,566, filed on Sep. 3, 1999, now abandoned, which is a continuation-in-part of application No. 08/856,141, filed on May 14, 1997, now Pat. No. 5,948,616.

(51) Int. Cl.$^7$ .......................... C12Q 1/68; C07H 21/04; C12P 19/34
(52) U.S. Cl. .......................... 435/6; 435/91.2; 536/23.5; 536/24.31; 536/24.33
(58) Field of Search ........................ 435/6, 7.1, 91.2; 536/23.5, 24.31, 24.33

(56) References Cited

U.S. PATENT DOCUMENTS

| | | | |
|---|---|---|---|
| 4,861,708 A | 8/1989 | Frossard | 435/6 |
| 5,359,045 A | 10/1994 | Soubrier et al. | 536/23.2 |

FOREIGN PATENT DOCUMENTS

| | | |
|---|---|---|
| EP | 0 297 913 B1 | 1/1989 |
| EP | 0 297 913 A3 | 3/1990 |
| WO | WO 87/02709 | 5/1987 |
| WO | 98/51822 | * 11/1998 |

OTHER PUBLICATIONS

Song et al. *Hum. Genet.* 99:727–734, 1997.
Friend et al. *Clinical and Experimental Pharmacology and Physiology* 23:564–566, Jun. 1996.
Zee et al. *Clinical and Experimental Pharmacology and Physiology* 21:925–930, 1994.
Sambrook et al. Molecular Cloning: A Laboratory manual. $2^{nd}$ Edition. Cold Spring Harbor Laboratory Press, New York, 1989.
Berge, K.E. and Berg, K. "No Effect of TaqI Polymorphism at the Human Renal Kallikrein (KLK1) Locus on Normal Blood Pressure Level or Variability" *Clin. Genet.* 44:196–202, 1993.
Richards et al. "Human Glandular Kallikrein Genes: Genetic and Physical Mapping of the KLK1 Locus Using a Highly Polymorphic Microsatellite PCR Marker" *Genomics* 11:77–82, 1991.
Pravenec et al. "Cosegregation of Blood Pressure with a Kallikrein Gene Family Polymorphism" *Hypertension* 17(2):242–246, Feb. 1991.
Woodley–Miller et al. "Restriction Fragment Length Polymorphisms Mapped in Spontaneously Hypertensive Rats Using Kallikrein Probes" *J. Hypertension* 7(11):865–871, 1989.
Berry et al. "A Gene for High Urinary Kallikrein May Protect Against Hypertension in Utah Kindreds" *Hypertension* 13(1):3–8, Jan. 1989.
Evans et al. "Structure and Chromosomal Localization of the Human Renal Kallikrein Gene" *Biochemistry* 27(9):3124–3129, 1988.

* cited by examiner

*Primary Examiner*—Carla J. Myers
(74) *Attorney, Agent, or Firm*—Needle & Rosenberg, P.C.

(57) ABSTRACT

The present invention provides a method of identifying a human subject as having an increased likelihood of regulating blood pressure with dietary sodium intake, comprising determining the presence in the subject of a tissue kallikrein promoter allele genotype correlated with an increased likelihood of regulating blood pressure with dietary sodium intake, whereby the presence of the genotype identifies the subject as having an increased likelihood of regulating blood pressure by dietary sodium intake. Also provided is a method of identifying a tissue kallikrein promoter allele genotype correlated with an increased likelihood of regulating blood pressure with dietary sodium intake, comprising a) determining the tissue kallikrein promoter allele genotype of a subject; and b) correlating the presence of the genotype of step (a) with the ability of the subject to regulate blood pressure by dietary sodium intake, thereby identifying a genotype correlated with an increased likelihood of regulating blood pressure by dietary sodium intake.

22 Claims, 9 Drawing Sheets

SEQUENCE LISTING

```
<160> NUMBER OF SEQ ID NOS: 31

<210> SEQ ID NO 1
<211> LENGTH: 17
<212> TYPE: DNA
<213> ORGANISM: Artificial Sequence
<220> FEATURE:
<223> OTHER INFORMATION: Description of Artificial Sequence:/Note =
      synthetic construct

<400> SEQUENCE: 1
ctgcaggaat ctagttc                                                        17

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence:/Note =
      synthetic construct

<400> SEQUENCE: 2
cagaaccagg aaccacat                                                       18

<210> SEQ ID NO 3
<211> LENGTH: 17
<212> TYPE: DNA
<213> ORGANISM: Artificial Sequence
<220> FEATURE:
<223> OTHER INFORMATION: Description of Artificial Sequence:/Note =
      synthetic construct

<400> SEQUENCE: 3
atctggaggc actagga                                                        17

<210> SEQ ID NO 4
<211> LENGTH: 17
<212> TYPE: DNA
<213> ORGANISM: Artificial Sequence
<220> FEATURE:
<223> OTHER INFORMATION: Description of Artificial Sequence:/Note =
      synthetic construct
```

```
<400> SEQUENCE: 4
tcctagtgcc tccagat                                                17

<210> SEQ ID NO 5
<211> LENGTH: 17
<212> TYPE: DNA
<213> ORGANISM: Artificial Sequence
<220> FEATURE:
<223> OTHER INFORMATION: Description of Artificial Sequence:/Note =
      synthetic construct

<400> SEQUENCE: 5
gtaccagggt cactgat                                                17

<210> SEQ ID NO 6
<211> LENGTH: 17
<212> TYPE: DNA
<213> ORGANISM: Artificial Sequence
<220> FEATURE:
<223> OTHER INFORMATION: Description of Artificial Sequence:/Note =
      synthetic construct

<400> SEQUENCE: 6
atcagtgacc ctggtac                                                17

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence:/Note =
      synthetic construct

<400> SEQUENCE: 7
gaatgcgtcc agcgtgatcc                                             20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence:/Note =
      synthetic construct

<400> SEQUENCE: 8
agcccttatc ccctcagagc                                             20

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence:/Note =
      synthetic construct

<400> SEQUENCE: 9
attctgggga tcggaggg                                               18

<210> SEQ ID NO 10
<211> LENGTH: 16
<212> TYPE: DNA
<213> ORGANISM: Artificial Sequence
<220> FEATURE:
<223> OTHER INFORMATION: Description of Artificial Sequence:/Note =
      synthetic construct

<400> SEQUENCE: 10
```

```
tctgggatc ggaggc                                                    16

<210> SEQ ID NO 11
<211> LENGTH: 17
<212> TYPE: DNA
<213> ORGANISM: Artificial Sequence
<220> FEATURE:
<223> OTHER INFORMATION: Description of Artificial Sequence:/Note =
      synthetic construct

<400> SEQUENCE: 11
gtgatccagg gcctgca                                                  17

<210> SEQ ID NO 12
<211> LENGTH: 17
<212> TYPE: DNA
<213> ORGANISM: Artificial Sequence
<220> FEATURE:
<223> OTHER INFORMATION: Description of Artificial Sequence:/Note =
      synthetic construct

<400> SEQUENCE: 12
cttcccctgt tgcctgg                                                  17

<210> SEQ ID NO 13
<211> LENGTH: 17
<212> TYPE: DNA
<213> ORGANISM: Artificial Sequence
<220> FEATURE:
<223> OTHER INFORMATION: Description of Artificial Sequence:/Note =
      synthetic construct

<400> SEQUENCE: 13
tggaggaact ggggaac                                                  17

<210> SEQ ID NO 14
<211> LENGTH: 14
<212> TYPE: DNA
<213> ORGANISM: Artificial Sequence
<220> FEATURE:
<223> OTHER INFORMATION: Description of Artificial Sequence:/Note =
      synthetic construct

<400> SEQUENCE: 14 ggagggggggg gggc                                                    14

<210> SEQ ID NO 15
<211> LENGTH: 14
<212> TYPE: DNA
<213> ORGANISM: Artificial Sequence
<220> FEATURE:
<223> OTHER INFORMATION: Description of Artificial Sequence:/Note =
      synthetic construct

<400> SEQUENCE: 15
ggaggcgggg gggc                                                     14

<210> SEQ ID NO 16
<211> LENGTH: 14
<212> TYPE: DNA
<213> ORGANISM: Artificial Sequence
<220> FEATURE:
<223> OTHER INFORMATION: Description of Artificial Sequence:/Note =
      synthetic construct

<400> SEQUENCE: 16
```

-continued

```
gggggggggg gggc                                                    14

<210> SEQ ID NO 17
<211> LENGTH: 14
<212> TYPE: DNA
<213> ORGANISM: Artificial Sequence
<220> FEATURE:
<223> OTHER INFORMATION: Description of Artificial Sequence:/Note =
      synthetic construct

<400> SEQUENCE: 17
ggggcggggg gggc                                                    14

<210> SEQ ID NO 18
<211> LENGTH: 14
<212> TYPE: DNA
<213> ORGANISM: Artificial Sequence
<220> FEATURE:
<223> OTHER INFORMATION: Description of Artificial Sequence:/Note =
      synthetic construct

<400> SEQUENCE: 18
ggagggcggg gggc                                                    14

<210> SEQ ID NO 19
<211> LENGTH: 15
<212> TYPE: DNA
<213> ORGANISM: Artificial Sequence
<220> FEATURE:
<223> OTHER INFORMATION: Description of Artificial Sequence:/Note =
      synthetic construct

<400> SEQUENCE: 19
ggagcggggg ggggc                                                   15

<210> SEQ ID NO 20
<211> LENGTH: 15
<212> TYPE: DNA
<213> ORGANISM: Artificial Sequence
<220> FEATURE:
<223> OTHER INFORMATION: Description of Artificial Sequence:/Note =
      synthetic construct

<400> SEQUENCE: 20
ggaggggggg ggggc                                                   15

<210> SEQ ID NO 21
<211> LENGTH: 13
<212> TYPE: DNA
<213> ORGANISM: Artificial Sequence
<220> FEATURE:
<223> OTHER INFORMATION: Description of Artificial Sequence:/Note =
      synthetic construct

<400> SEQUENCE: 21 ggagggggggg ggc                                                    13

<210> SEQ ID NO 22
<211> LENGTH: 16
<212> TYPE: DNA
<213> ORGANISM: Artificial Sequence
<220> FEATURE:
<223> OTHER INFORMATION: Description of Artificial Sequence:/Note =
      synthetic construct

<400> SEQUENCE: 22 ggagggggggg ggggc                                                  16
```

```
<210> SEQ ID NO 23
<211> LENGTH: 13
<212> TYPE: DNA
<213> ORGANISM: Artificial Sequence
<220> FEATURE:
<223> OTHER INFORMATION: Description of Artificial Sequence:/Note =
      synthetic construct

<400> SEQUENCE: 23
ggagggcggg ggc                                                          13

<210> SEQ ID NO 24
<211> LENGTH: 14
<212> TYPE: DNA
<213> ORGANISM: Artificial Sequence
<220> FEATURE:
<223> OTHER INFORMATION: Description of Artificial Sequence:/Note =
      synthetic construct

<400> SEQUENCE: 24
ggagcggggg gggc                                                         14

<210> SEQ ID NO 25
<211> LENGTH: 12
<212> TYPE: DNA
<213> ORGANISM: Artificial Sequence
<220> FEATURE:
<223> OTHER INFORMATION: Description of Artificial Sequence:/Note =
      synthetic construct

<400> SEQUENCE: 25
ggaggggggg gc                                                           12

<210> SEQ ID NO 26
<211> LENGTH: 17
<212> TYPE: DNA
<213> ORGANISM: Artificial Sequence
<220> FEATURE:
<223> OTHER INFORMATION: Description of Artificial Sequence:/Note =
      synthetic construct

<400> SEQUENCE: 26 ggagggggggg gggggc                                                      17

<210> SEQ ID NO 27
<211> LENGTH: 16
<212> TYPE: DNA
<213> ORGANISM: Artificial Sequence
<220> FEATURE:
<223> OTHER INFORMATION: Description of Artificial Sequence:/Note =
      synthetic construct

<400> SEQUENCE: 27 ggagggggggg ggcggc                                                      16

<210> SEQ ID NO 28
<211> LENGTH: 13
<212> TYPE: DNA
<213> ORGANISM: Artificial Sequence
<220> FEATURE:
<223> OTHER INFORMATION: Description of Aritficial Sequence:/Note =
      synthetic construct

<400> SEQUENCE: 28
gggggggggg ggc                                                          13
```

```
<210> SEQ ID NO 29
<211> LENGTH: 20
<212> TYPE: DNA
<213> ORGANISM: Artificial Sequence
<220> FEATURE:
<223> OTHER INFORMATION: Description of Aritficial Sequence:/Note =
      synthetic construct

<400> SEQUENCE: 29
gaatgcgtcc agcgtgatcc                                                     20

<210> SEQ ID NO 30
<211> LENGTH: 20
<212> TYPE: DNA
<213> ORGANISM: Artificial Sequence
<220> FEATURE:
<223> OTHER INFORMATION: Description of Aritficial Sequence:/Note =
      synthetic construct

<400> SEQUENCE: 30
agcccttatc ccctcagagc                                                     20

<210> SEQ ID NO 31
<211> LENGTH: 17
<212> TYPE: DNA
<213> ORGANISM: Artificial Sequence
<220> FEATURE:
<223> OTHER INFORMATION: Description of Aritficial Sequence:/Note =
      synthetic construct

<400> SEQUENCE: 31
gtgatccagg gcctgca                                                        17
```

METHODS AND COMPOSITIONS FOR CORRELATING TISSUE KALLIKREIN GENE PROMOTER POLYMORPHISMS WITH TREATMENT OF ESSENTIAL HYPERTENSION

The present application is a continuation-in-part application of, and claims priority to, U.S. Ser. No. 09/389,566, filed Sep. 3, 1999, pending, which is a continuation-in-part application of U.S. Ser. No. 08/856,141, filed May 14, 1997, now U.S. Pat. No. 5,948,616, issued Sep. 7, 1999.

This invention was made with government support under the National Institutes of Health grant numbers HL 29397 and HL 44083. The government has certain rights in this invention.

BACKGROUND ART

1. Field of the Invention

The present invention provides methods and compositions for identifying human subjects with an increased risk of having essential hypertension. In particular, this invention relates to the identification and characterization of polymorphisms in the human tissue kallikrein gene promoter correlated with increased or decreased risk of developing essential hypertension and the responsiveness of a subject to various treatments for hypertension.

2. Background Art

The tissue kallikrein-kinin system has long been implicated in blood pressure regulation by genetic and physiological studies. Urinary excretion of tissue kallikrein is significantly lower in patients with essential hypertension (Elliot et al., 1934; Carretero et al., 1971; Margolius et al., 1971; Margolius et al., 1974) and in genetically hypertensive rats (Carretero et al., 1976; Carretero et al., 1978; Ader et al., 1986; Ader et al., 1987). Total urinary tissue kallikrein excretion was also found to be lower among individuals with parental hypertension than it was in individuals with two normotensive parents (Williams et al, 1987). Transgenic mice over-expressing the human tissue kallikrein gene have been shown to exhibit a hypotensive phenotype (Wang et al., 1994; Song et al., 1995). Further, a study involving 57 Utah pedigrees indicates that a dominant allele expressed as high total urinary kallikrein excretion may be associated with decreased risk of essential hypertension (Berry et al., 1989).

Identification of DNA polymorphisms provides an efficient way to study the association of genes and diseases by linkage analysis. The human tissue kallikrein gene is located on the long arm of chromosome 19 q13.3–13.4 (Evans et al., 1988). Although a TaqI restriction fragment length polymorphism (RFLP) was found at this locus in a Norwegian population (Berge and Berg, 1991), this genetic marker has only two polymorphisms with unfavored allelic frequencies, making it unsuitable for genetic studies. No significant linkage was found between blood pressure and the kallikrein gene using this marker (Berge and Berg, 1993). A polymorphic microsatellite marker close to the tissue kallikrein gene locus has been identified which is useful for linkage analysis (Richards et al., 1991). However, no previous studies have demonstrated a correlation between specific polymorphisms in the tissue kallikrein gene and blood pressure.

A major challenge in the hypertension field is the development and implementation of rational therapeutic approaches and new preventive measures. High blood pressure is associated with the risk of coronary heart disease and stroke not only among "hypertensive" patients, but also among "normotensive" individuals (MacMahon et al., 1990). A reduction of 5 mmHg in diastolic blood pressure could result in a 21% reduced risk for coronary heart disease and 34% for stroke (MacMahon et al., 1990). Because a universal salt restriction may be inappropriate at the population level due to the heterogeneity of blood pressure responses (Pecker and Laragh, 1991), the need exists for a marker to predict blood pressure responsive variations with regard to particular clinical treatments. A link between kallikrein promoter polymorphism, urinary kallikrein level, salt sensitivity and blood pressure response would have great utility in categorizing individuals for particular clinical treatments, such as a preferential low salt recommendation for salt-sensitive patients, and a directional selection of anti-hypertensive drugs [e.g., diuretics and angiotension-converting enzyme (ACE) inhibitors] according to a patient's genotype.

The present invention overcomes previous shortcomings in the art by providing methods and compositions for identifying individuals having an increased or decreased risk of developing essential hypertension and identifying the responsiveness of individuals to certain treatment modalities, based on analysis and characterization of a highly polymorphic locus in the promoter region of the human tissue kallikrein gene.

SUMMARY OF THE INVENTION

The present invention provides a method for identifying a human subject as having an increased risk of developing essential hypertension, comprising determining the presence in the subject of an allele in the promoter region of the subject's tissue kallikrein gene correlated with an increased risk of developing essential hypertension, the presence of the allele identifying the subject as having an increased risk of developing essential hypertension.

Also provided is a method for identifying a human subject as having an increased risk of developing essential hypertension, comprising correlating the presence of a nucleic acid sequence at nucleotides −166 through −98 in a human tissue kallikrein gene with an increased risk of developing essential hypertension; and determining the nucleic acid sequence of nucleotides −166 through −98 of the subject's tissue kallikrein gene, whereby a subject having a nucleic acid sequence at nucleotides −166 through −98 in the tissue kallikrein gene correlated with an increased risk of developing essential hypertension is identified as having an increased risk of developing essential hypertension.

Furthermore, a method of identifying an allele in the promoter region of the human tissue kallikrein gene correlated with an increased risk of developing essential hypertension is also provided, comprising determining the nucleic acid sequence of the nucleotides at positions −166 through −98 in the human tissue kallikrein gene from a subject; and correlating the presence of the nucleic acid sequence of the subject with the diagnosis of essential hypertension in the subject, whereby the nucleic acid sequence of the nucleotides at positions −166 through −98 in the promoter region of the human tissue kallikrein gene identifies an allele correlated with an increased risk of developing essential hypertension.

Additionally provided is a method of identifying an allele in the promoter region of a human tissue kallikrein gene correlated with an increased risk of developing essential hypertension, comprising determining the nucleic acid sequence of the nucleotides at positions −166 through −98 in the promoter region of the human tissue kallikrein gene; cloning the nucleic acid sequence encoding the promoter region of the human tissue kallikrein gene into an expression vector having a reporter gene; expressing the reporter gene to produce a gene product under the direction of the promoter region of the human tissue kallikrein gene; and determining the amount of reporter gene product produced, an amount of reporter gene product less than the amount of reporter gene product produced under the direction of a tissue kallikrein gene promoter containing the nucleotide sequence of SEQ ID NO:14 (allele A) or the nucleotide sequence of SEQ ID NO:15 (allele B) identifying a nucleic acid sequence of the nucleotides at position −166 through −98 of the human tissue kallikrein gene as an allele correlated with an increased risk of developing essential hypertension.

Further provided is a method for identifying a human subject as having an increased risk of developing essential hypertension, comprising cloning the nucleic acid sequence encoding the promoter region of the human tissue kallikrein gene of the subject into an expression vector having a reporter gene; expressing the reporter gene to produce a gene product under the direction of the promoter region of the human tissue kallikrein gene; and determining the amount of reporter gene product produced, an amount of reporter gene product less than the amount of reporter gene product produced under the direction of a tissue kallikrein gene promoter containing the nucleotide sequence of SEQ ID NO:14 (allele A) or the nucleotide sequence of SEQ ID NO:15 (allele B) identifying a subject as having an increased risk of developing essential hypertension.

In addition, a method for identifying an allele in the promoter region of the human tissue kallikrein gene is provided, comprising determining the nucleic acid sequence of the nucleotides at positions −166 through −98.

The present invention further provides an isolated nucleic acid consisting of the promoter region of the human tissue kallikrein gene between positions −1 to −940, the complementary sequence of the isolated nucleic acid, vectors containing the nucleic acid and cells expressing the vector.

The present invention also provides a method of identifying a subject at reduced risk of having essential hypertension, comprising determining the presence in the subject of an allele in the promoter region of the subject's tissue kallikrein gene correlated with a reduced risk of developing essential hypertension, the presence of the allele identifying the subject as having a reduced risk of developing essential hypertension.

Additionally provided in the present invention is a method for identifying a human subject as having a reduced risk of developing essential hypertension, comprising correlating the presence of a nucleic acid sequence at nucleotides −166 through −98 in a human tissue kallikrein gene with a reduced risk of developing essential hypertension; and determining the nucleic acid sequence of nucleotides −166 through −98 of the subject's tissue kallikrein gene, whereby a subject having a nucleic acid sequence at nucleotides −166 through −98 in the tissue kallikrein gene correlated with a reduced risk of developing essential hypertension is identified as having a reduced risk of developing essential hypertension.

A method is also provided for identifying an allele in the promoter region of the human tissue kallikrein gene correlated with a reduced risk of developing essential hypertension comprising determining the nucleic acid sequence of the nucleotides at positions −166 through −98 in the human tissue kallikrein gene from a subject; and correlating the presence of the nucleic acid sequence of the subject with the absence of essential hypertension in the subject, whereby the nucleic acid sequence of the nucleotides at positions −166 through −98 in the promoter region of the human tissue kallikrein gene identifies an allele correlated with a reduced risk of developing essential hypertension.

The present invention further provides a method of identifying an allele in the promoter region of a human tissue kallikrein gene correlated with a reduced risk of developing essential hypertension, comprising determining the nucleic acid sequence of the nucleotides at positions −166 through −98 in the promoter region of the human tissue kallikrein gene; cloning the nucleic acid sequence encoding the promoter region of the human tissue kallikrein gene into an expression vector having a reporter gene; expressing the reporter gene to produce a gene product under the direction of the promoter region of the human tissue kallikrein gene; and determining the amount of reporter gene product produced, an amount of reporter gene product greater than the amount of reporter gene product produced under the direction of a tissue kallikrein gene promoter containing the nucleotide sequence of SEQ ID NO:14 (allele A) or the nucleotide sequence of SEQ ID NO:15 (allele B) identifying a nucleic acid sequence of the nucleotides at position −166 through −98 of the human tissue kallikrein gene as an allele correlated with a reduced risk of developing essential hypertension.

Also provided is a method for identifying a human subject as having a reduced risk of developing essential hypertension, comprising cloning the nucleic acid sequence encoding the promoter region of the human tissue kallikrein gene of the subject into an expression vector having a reporter gene; expressing the reporter gene to produce a gene product under the direction of the promoter region of the human tissue kallikrein gene; and determining the amount of reporter gene product produced, an amount of reporter gene product greater than the amount of reporter gene product produced under the direction of a tissue kallikrein gene promoter containing the nucleotide sequence of SEQ ID NO:14 (allele A) or the nucleotide sequence of SEQ ID NO:15 (allele B) identifying a subject as having a reduced risk of developing essential hypertension.

In addition to the embodiments described above, the present invention provides a method of identifying a human subject as having an increased likelihood of regulating blood pressure with dietary sodium intake, comprising determining the presence in the subject of a tissue kallikrein promoter allele genotype correlated with an increased likelihood of regulating blood pressure with dietary sodium intake, whereby the presence of the genotype identifies the subject as having an increased likelihood of regulating blood pressure by dietary sodium intake.

Additionally provided in this invention is a method of identifying a human subject as having an increased likelihood of regulating blood pressure with dietary sodium intake, comprising a) correlating the presence of a tissue kallikrein promoter allele genotype with an increased likelihood of regulating blood pressure with dietary sodium intake; and b) determining the tissue kallikrein promoter allele genotype of the subject, whereby a subject having a tissue kallikrein promoter allele genotype correlated with an increased likelihood of regulating blood pressure with dietary sodium intake is identified as having an increased likelihood of regulating blood pressure with dietary sodium intake.

Furthermore, a method is provided for identifying a tissue kallikrein promoter allele genotype correlated with an increased likelihood of regulating blood pressure with dietary sodium intake, comprising a) determining the tissue kallikrein promoter allele genotype of a subject; and b) correlating the presence of the genotype of step (a) with the ability of the subject to regulate blood pressure by dietary sodium intake, thereby identifying a genotype correlated with an increased likelihood of regulating blood pressure by dietary sodium intake.

Additionally, the present invention provides a method for identifying a human subject as having a reduced likelihood of regulating blood pressure with dietary sodium intake, comprising determining the presence in the subject of a tissue kallikrein promoter allele genotype correlated with a reduced likelihood of regulating blood pressure with dietary sodium intake, whereby the presence of the genotype identifies the subject as having a reduced likelihood of regulating blood pressure with dietary sodium intake.

Additionally provided in this invention is a method of identifying a human subject as having a reduced likelihood of regulating blood pressure with dietary sodium intake, comprising a) correlating a tissue kallikrein promoter allele genotype with a reduced likelihood of regulating blood pressure with dietary sodium intake; and b) determining the tissue kallikrein promoter allele genotype of the subject, whereby a subject having a tissue kallikrein promoter allele genotype correlated with a reduced likelihood of regulating blood pressure with dietary sodium intake is identified as having a reduced likelihood of regulating blood pressure with dietary sodium intake.

Also, a method is provided of identifying a tissue kallikrein promoter allele genotype correlated with a reduced likelihood of regulating blood pressure with dietary sodium intake, comprising a) determining the tissue kallikrein promoter allele genotype of a subject; and b) correlating the presence of the genotype of step (a) with the inability of the subject to regulate blood pressure by dietary sodium intake, thereby identifying the genotype correlated with a reduced likelihood of regulating blood pressure by dietary sodium intake.

In a further embodiment, the present invention provides a method of identifying a human subject as having an increased likelihood of regulating blood pressure with a diuretic, comprising determining the presence in the subject of a tissue kallikrein promoter allele genotype correlated with an increased likelihood of regulating blood pressure with a diuretic, whereby the presence of the genotype identifies the subject as having an increased likelihood of regulating blood pressure with a diuretic.

Additionally provided is a method of identifying a human subject as having an increased likelihood of regulating blood pressure with a diuretic, comprising a) correlating the presence of a tissue kallikrein promoter allele genotype with an increased likelihood of regulating blood pressure with a diuretic; and b) determining the tissue kallikrein promoter allele genotype of the subject, whereby a subject having a tissue kallikrein promoter allele genotype correlated with an increased likelihood of regulating blood pressure with a diuretic is identified as having an increased likelihood of regulating blood pressure with a diuretic.

Also provided herein is a method of identifying a tissue kallikrein promoter allele genotype correlated with an increased likelihood of regulating blood pressure with a diuretic, comprising a) determining the tissue kallikrein promoter allele genotype of a subject; and b) correlating the presence of the genotype of step (a) with the ability of the subject to regulate blood pressure with a diuretic, thereby identifying a genotype correlated with an increased likelihood of regulating blood pressure with a diuretic.

A method of identifying a human subject as having a reduced likelihood of regulating blood pressure with a diuretic is also provided, comprising determining the presence in the subject of a tissue kallikrein promoter allele genotype correlated with a reduced likelihood of regulating blood pressure with a diuretic, whereby the presence of the genotype identifies the subject as having a reduced likelihood of regulating blood pressure with a diuretic.

Furthermore, the present invention provides a method of identifying a human subject as having a reduced likelihood of regulating blood pressure with a diuretic, comprising a) correlating a tissue kallikrein promoter allele genotype with a reduced likelihood of regulating blood pressure with a diuretic; and b) determining the tissue kallikrein promoter allele genotype of the subject, whereby a subject having a tissue kallikrein promoter allele genotype correlated with a reduced likelihood of regulating blood pressure with a diuretic is identified as having a reduced likelihood of regulating blood pressure with a diuretic.

Also provided is a method of identifying a tissue kallikrein promoter allele genotype correlated with a reduced likelihood of regulating blood pressure with a diuretic, comprising a) determining the tissue kallikrein promoter allele genotype of a subject; and b) correlating the presence of the genotype of step (a) with the inability of the subject to regulate blood pressure with a diuretic, thereby identifying the genotype as correlated with a reduced likelihood of regulating blood pressure with a diuretic.

The present invention additionally provides a method of identifying a human subject as having an increased likelihood of regulating blood pressure with an angiotensin-converting enzyme inhibitor, comprising determining the presence in the subject of a tissue kallikrein promoter allele genotype correlated with an increased likelihood of regulating blood pressure with an angiotensin-converting enzyme inhibitor, whereby the presence of the genotype identifies the subject as having an increased likelihood of regulating blood pressure with an angiotensin-converting enzyme inhibitor.

Furthermore, the present invention provides a method of identifying a human subject as having an increased likelihood of regulating blood pressure with an angiotensin-converting enzyme inhibitor, comprising a) correlating the presence of a tissue kallikrein promoter allele genotype with an increased likelihood of regulating blood pressure with an angiotensin-converting enzyme inhibitor; and b) determining the tissue kallikrein promoter allele genotype of the subject, whereby a subject having a tissue kallikrein promoter allele genotype correlated with an increased likelihood of regulating blood pressure with an angiotensin-converting enzyme inhibitor is identified as having an increased likelihood of regulating blood pressure with an angiotensin-converting enzyme inhibitor.

Also provided herein is a method of identifying a tissue kallikrein promoter allele genotype correlated with an increased likelihood of regulating blood pressure with an angiotensin-converting enzyme inhibitor, comprising a) determining the tissue kallikrein promoter allele genotype of a subject; and b) correlating the presence of the genotype of step (a) with the ability of the subject to regulate blood pressure with an angiotensin-converting enzyme inhibitor, thereby identifying a genotype correlated with an increased likelihood of regulating blood pressure with an angiotensin-converting enzyme inhibitor.

A method of identifying a human subject as having a reduced likelihood of regulating blood pressure with an angiotensin-converting enzyme inhibitor is additionally provided, comprising determining the presence in the subject of a tissue kallikrein promoter allele genotype correlated with a reduced likelihood of regulating blood pressure with an angiotensin-converting enzyme inhibitor, whereby the presence of the genotype identifies the subject as having a reduced likelihood of regulating blood pressure with an angiotensin-converting enzyme inhibitor.

In addition to the above embodiments, the present invention also provides a method of identifying a human subject as having a reduced likelihood of regulating blood pressure with an angiotensin-converting enzyme inhibitor, comprising a) correlating a tissue kallikrein promoter allele genotype with a reduced likelihood of regulating blood pressure with an angiotensin-converting enzyme inhibitor; and b) determining the tissue kallikrein promoter allele genotype of the subject, whereby a subject having a tissue kallikrein promoter allele genotype correlated with a reduced likelihood of regulating blood pressure with an angiotensin-converting enzyme inhibitor is identified as having a reduced likelihood of regulating blood pressure with an angiotensin-converting enzyme inhibitor.

Finally, the present invention provides a method of identifying a tissue kallikrein promoter allele genotype correlated with a reduced likelihood of regulating blood pressure with an angiotensin-converting enzyme inhibitor, comprising a) determining the tissue kallikrein promoter allele genotype of a subject; and b) correlating the presence of the genotype of step (a) with the inability of the subject to regulate blood pressure with an angiotensin-converting enzyme inhibitor, thereby identifying the genotype as correlated with a reduced likelihood of regulating blood pressure with an angiotensin-converting enzyme inhibitor.

Various other objectives and advantages of the present invention will become apparent from the following description.

These data also demonstrate that, under an unrestricted salt diet, people with BB genotype (or with B allele) have high renal kallikrein content, resulting in greater kinin production. As kinin is a diuretic and natriuretic, using diuretic drugs on these individuals would not be effective. However, ACE inhibitors would be very useful because ACE inhibitors can prevent kinin degradation (in addition to their ability to prevent angiotensin II formation).

Conversely, under a normal salt diet, people with the genotypes of 16/14 have low renal kallikrein content and they should benefit from diuretic drugs because they do not make much of the diuretics, kallikrein and kinin. These individuals would not benefit from ACE inhibitors in the same manner as people carrying the B allele because people with the 16/14 genotype will not have much kinin to accumulate even if the degradation of kinin is prevented.

Figure 4:
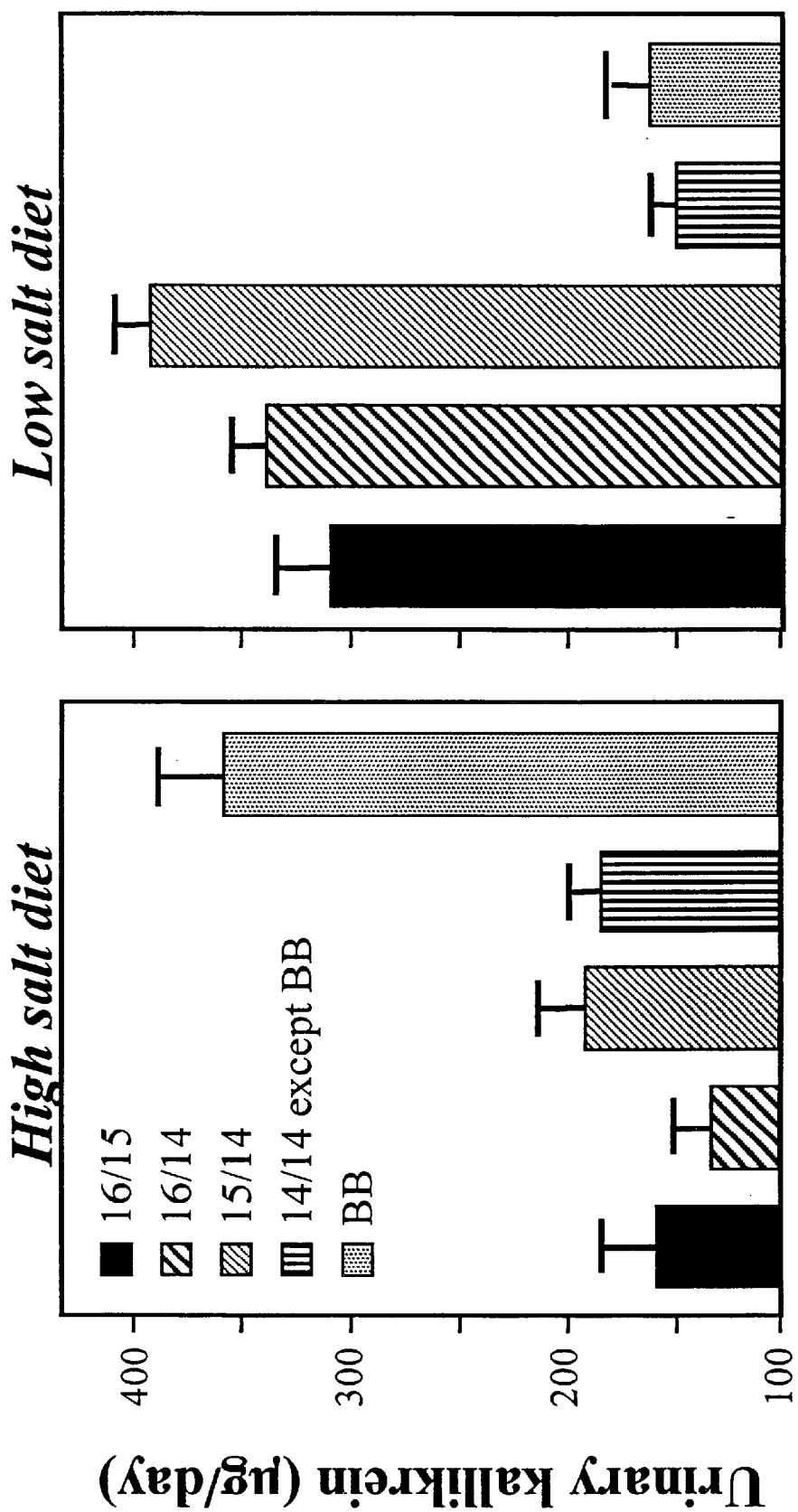
FIG. 4. Effects of kallikrein genotype and dietary salt intake on urinary kallikrein excretion. Due to the low frequency of certain alleles among the testing subjects, alleles of identical length are combined to achieve statistical significance. The number of subjects with BB genotype is large enough for it to be listed separately. These data demonstrate a strong linkage between tissue kallikrein genotype and dietary salt intake on urine kallikrein excretion. Because high urinary kallikrein level has a protective effect against the development of hypertension, individuals with genotypes of 16/15, 16/14 and 15/14 can benefit from a low salt diet. Individuals with 14/14 genotype (except BB genotype) are indifferent to either a high or low sodium diet. Individuals with BB genotype may even benefit from a high sodium diet.

As used in FIG. 4, 16=allele K and/or allele R (both are 16 nucleotides in length); 15=allele F and/or allele H (both are 15 nucleotides in length); and 14=allele A, allele B, allele C, allele D, allele E and/or allele G (all are 14 nucleotides in length; see Table 1). Thus, genotype 16/15 can be allele K/allele F, allele K/allele H, allele R/allele F and/or allele R/allele H. Genotype 16/14 can be allele K/allele A, allele K/allele B, allele K/allele C, allele K/allele D, allele K/allele E, allele K/allele G, allele R/allele A, allele R/allele B, allele R/allele C, allele R/allele D, allele R/allele E and/or allele R/allele G. Genotype 15/14 can be allele F/allele A, allele F/allele B, allele F/allele C, allele F/allele D, allele F/allele E, allele F/allele G, allele H/allele A, allele H/allele B, allele H/allele C, allele H/allele D, allele H/allele E and/or allele H/allele G. Genotype 14/14 can be allele A/allele A, allele A/allele B, allele A/allele C, allele A/allele D, allele A/allele E, allele A/allele G, allele B/allele C, allele B/allele D, allele B/allele E, allele B/allele G, allele C/allele C, allele C/allele D, allele C/allele E, allele C/allele G, allele D/allele D, allele D/allele E, allele D/allele G, allele E/allele E, allele E/allele G and/or allele G/allele G. Also as used in this application, high dietary salt means normal (i.e., unrestricted) sodium intake of about 50 to 100 millimoles of sodium per day and low dietary salt means sodium intake of no more than 10 millimoles of sodium per day. The parameters of high or low dietary salt intake as used in experimental studies such as those described herein are standard in the art.

Figure 5:
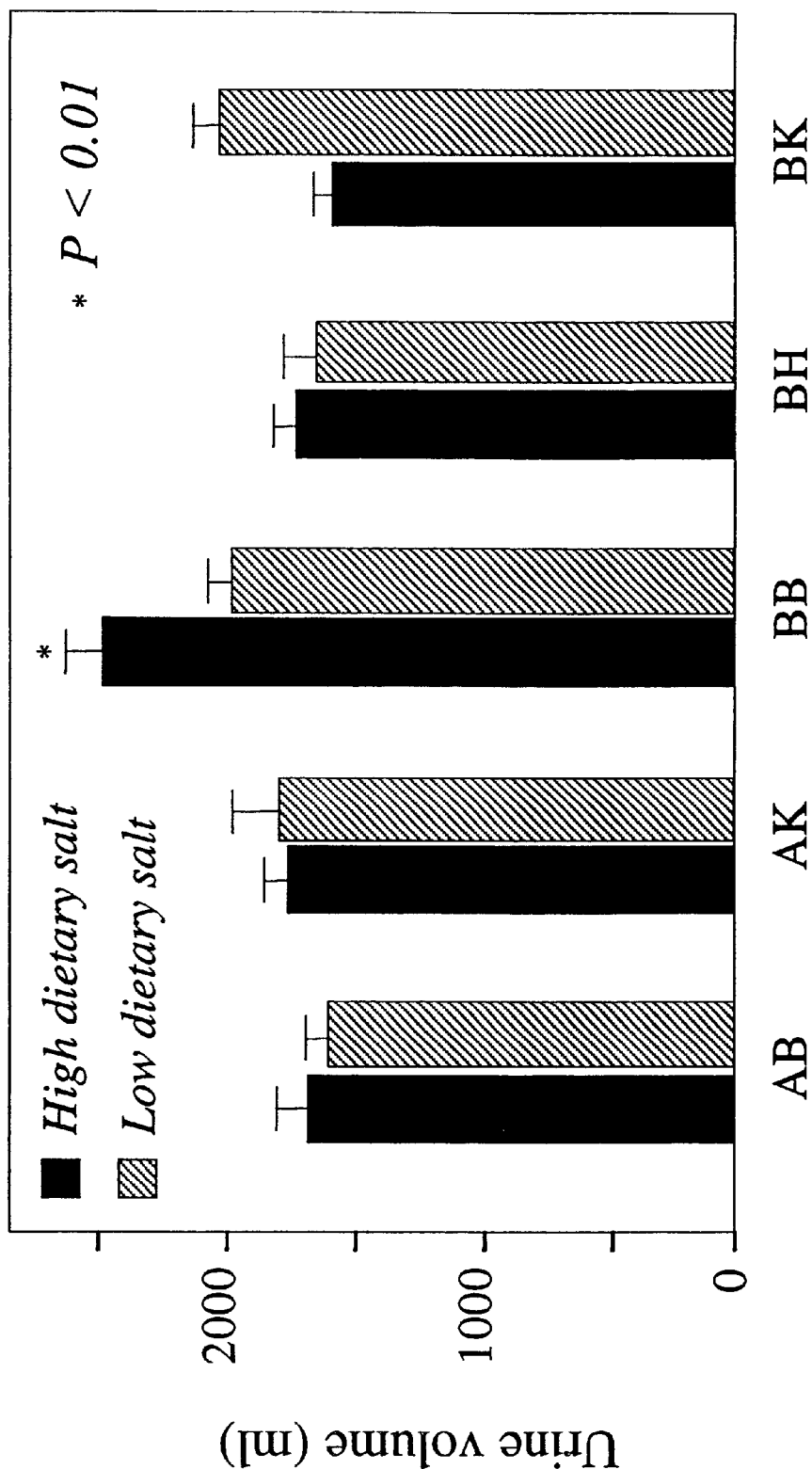

FIG. 5. Effects of kallikrein genotype and dietary salt on urine volume. Each bar shows a mean of the urine volume for various kallikrein genotypes. The values are expressed as mean±SEM. Solid bars, under unrestricted sodium diet; shaded bars, under restricted sodium diet. These data demonstrate a strong linkage between tissue kallikrein genotype and urine volume and also that the BB genotype confers the benefit of having a higher diuretic activity than other genotypes.

Figure 6:
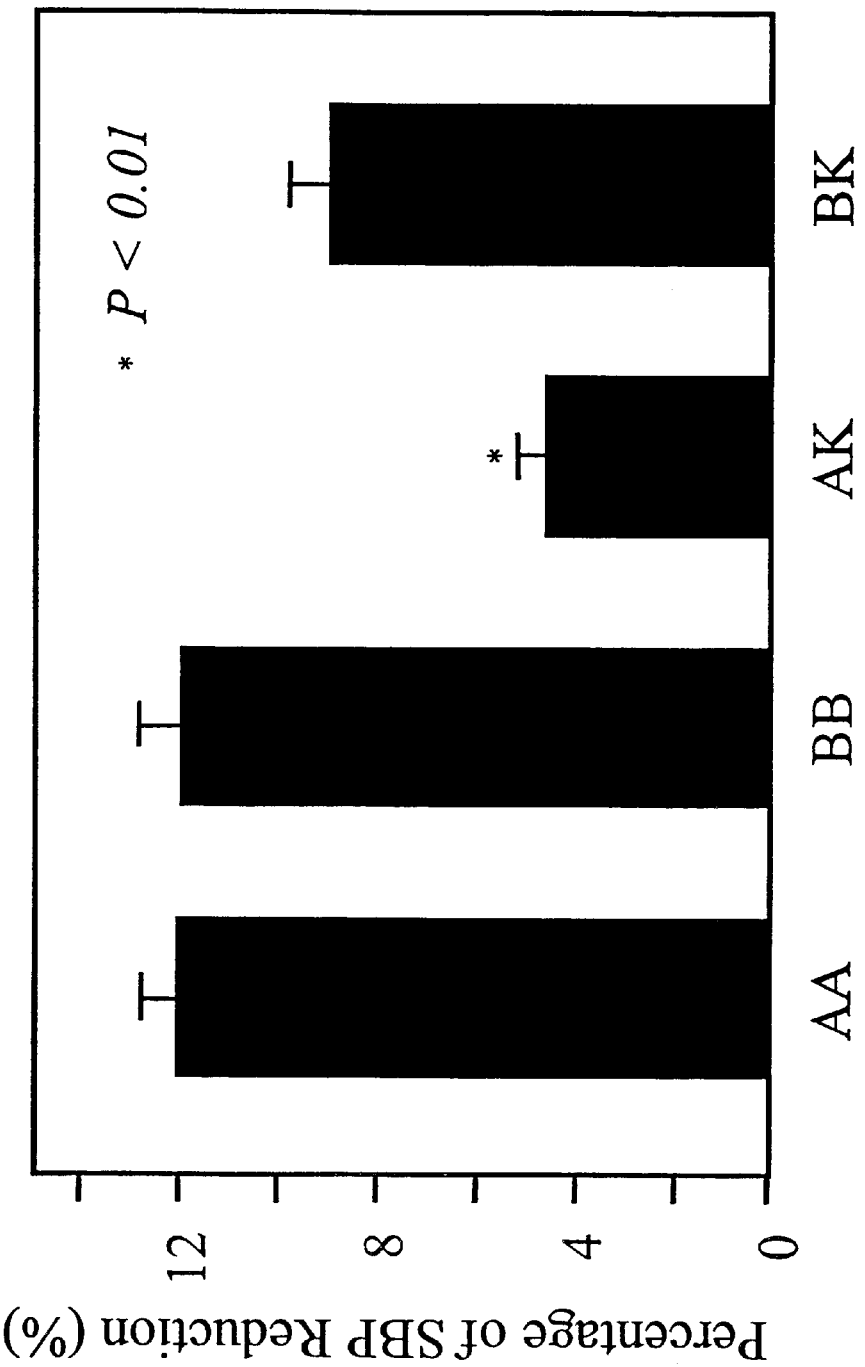

FIG. 6. Effects of kallikrein genotype on systolic blood pressure (SBP) reduction in response to dietary salt restriction. Each bar shows a mean of systolic blood pressure changes recorded by the percentage of reduction for various kallikrein genotypes. Values are expressed as mean±SEM.

These data show a strong linkage between tissue kallikrein genotype and blood pressure reduction in response to restricted dietary salt intake. As shown in the figure, the K allele confers poor blood pressure reduction response to restricted salt intake when in combination with the A allele (K allele is dominant over A allele). The B allele can rescue the K allele by improving blood pressure reduction response to restricted salt intake.

Figure 7:
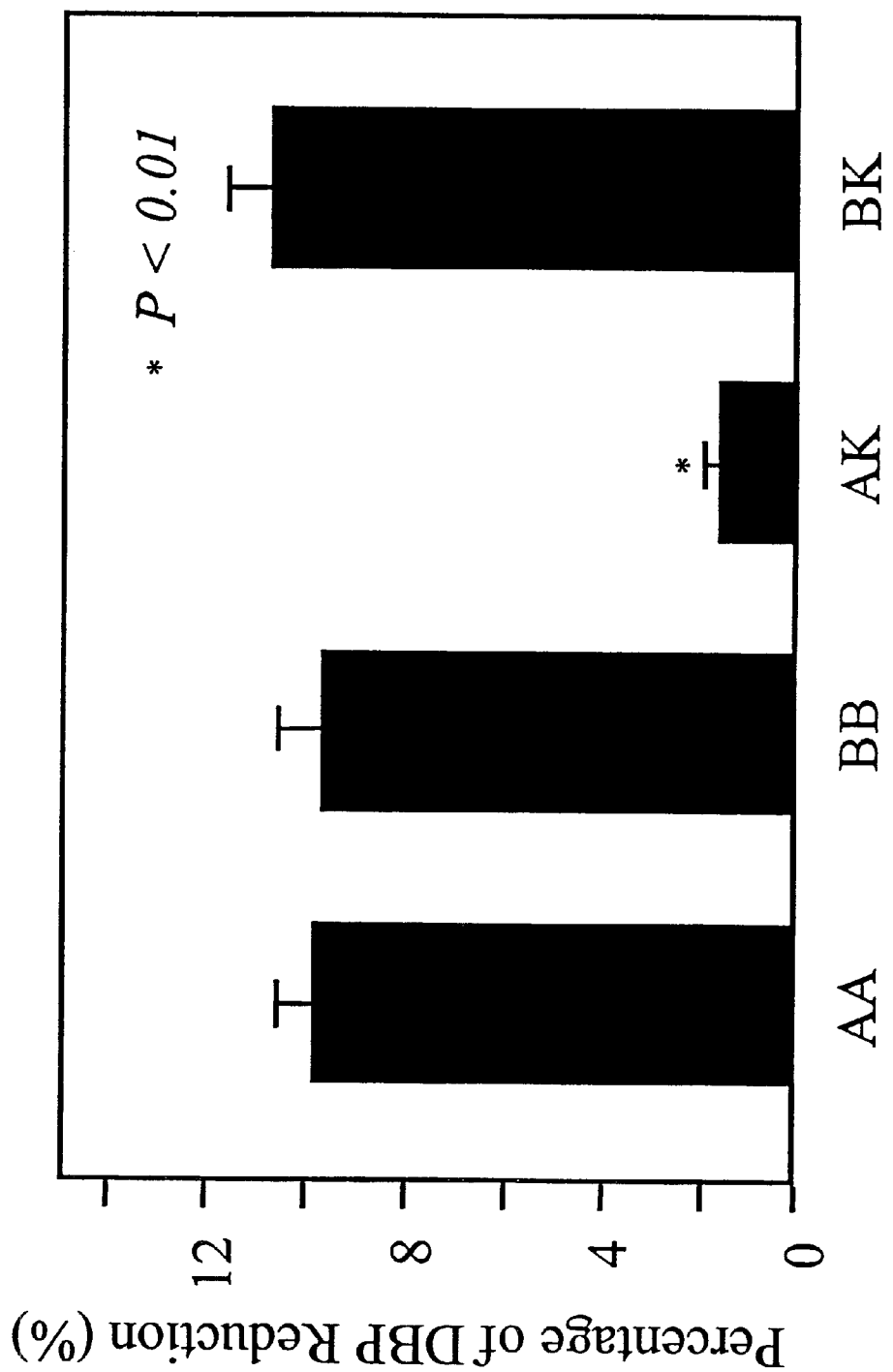

FIG. 7. Effects of kallikrein genotype on diastolic blood pressure (DBP) reduction in response to dietary salt restriction. Each bar shows a mean of diastolic blood pressure changes recorded by the percentage of reduction for various kallikrein genotypes. Values are expressed as mean±SEM.

These data show a strong linkage between tissue kallikrein genotype and blood pressure reduction in response to restricted dietary salt intake. As shown in the figure, the K allele confers poor blood pressure reduction response to restricted salt intake when in combination with the A allele (K allele is dominant over A allele). The B allele can rescue the K allele by improving blood pressure reduction response to restricted salt intake.

Figure 8A:
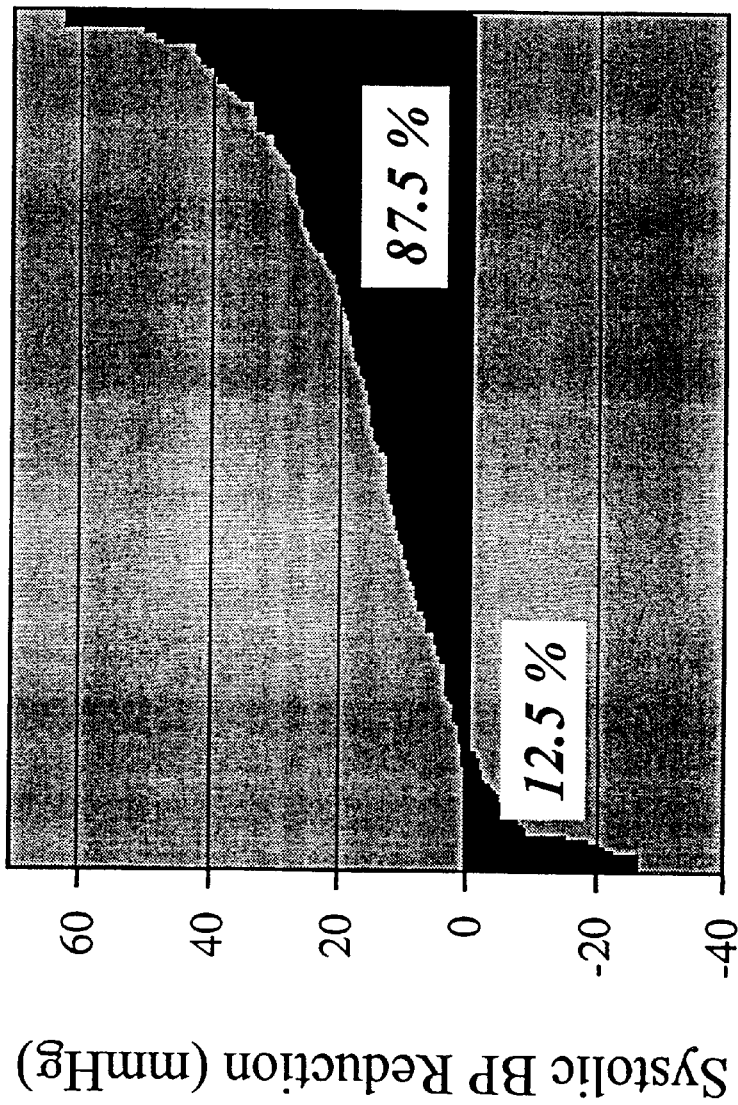
Figure 8B:
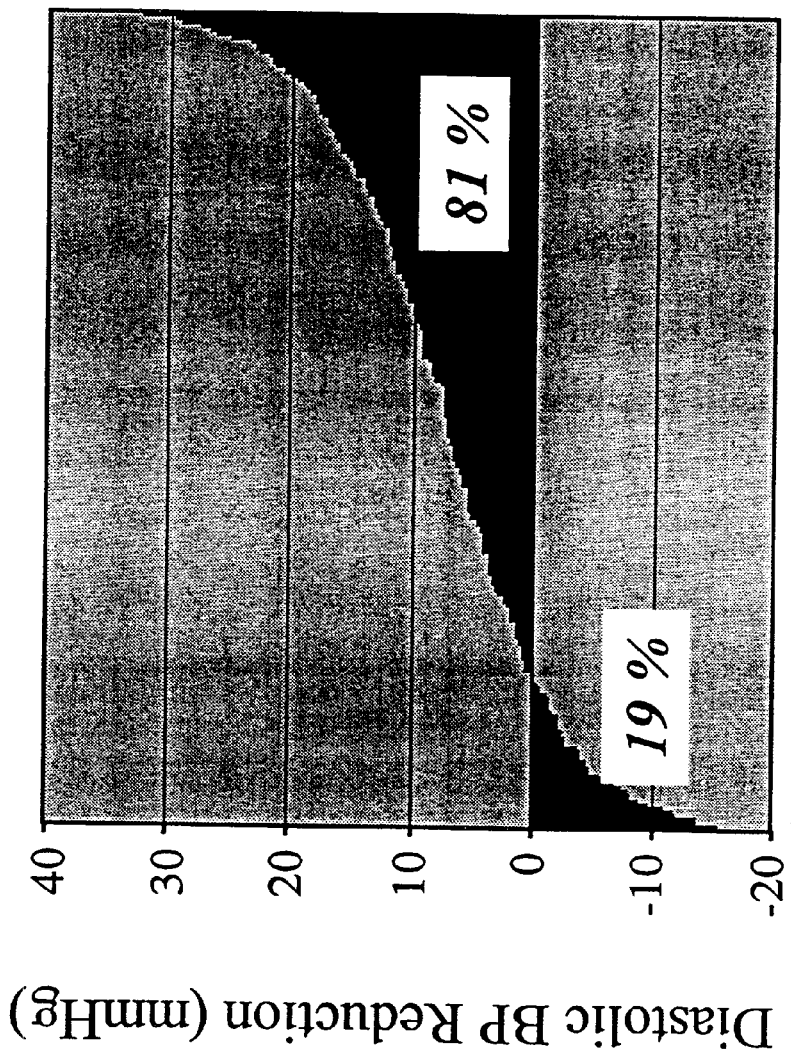

FIGS. 8A & 8B. Blood pressure reduction after dietary sodium restriction. The shaded area represents the percentage of these samples for the various responses to dietary sodium restriction. FIG. 8A shows systolic blood pressure. FIG. 8B shows diastolic blood pressure.

DETAILED DESCRIPTION OF THE INVENTION

As used in the claims, "a" can include multiples.

This invention provides a method for identifying a human subject as having an increased risk of developing essential hypertension, comprising determining the presence in the subject of an allele in the promoter region of the subject's tissue kallikrein gene correlated with an increased risk of developing essential hypertension, the presence of the allele identifying the subject as having an increased risk of developing essential hypertension. The presence of an allele is determined by isolating the promoter region of the subject's tissue kallikrein gene and determining the nucleic acid sequence of the promoter according to standard molecular biology protocols well known in the art as described for example in Sambrook et al. (1989) and as set forth in the Examples provided herein. The nucleic acid sequences of examples of the alleles of the present invention are set forth in Table 1.

An allele in the promoter region of the human tissue kallikrein gene can be identified as correlated with an increased risk of developing essential hypertension on the basis of statistical analyses of the incidence of a particular allele in individuals diagnosed with essential hypertension. Furthermore, an allele in the promoter region of the human kallikrein gene can be identified as an allele correlated with an increased risk of developing essential hypertension on the basis of statistical analysis of the incidence of a particular allele in individuals demonstrating a decrease in the amount of urinary excretion of tissue kallikrein relative to the average amount of urinary excretion of tissue kallikrein in a large sample of normotensive individuals. For example, the amount of tissue kallikrein excreted in the urine by subjects who have specific alleles can be determined according to methods well known in the art as described herein as well as in, for example, Shimamoto et al (1984). The amount of tissue kallikrein excreted in the urine by subjects diagnosed with essential hypertension can be determined as described herein. The data provided for these parameters can be used to establish a correlation between a specific allele in the promoter region of the human tissue kallikrein gene (genotype) and an increased risk of developing essential hypertension (phenotype).

In addition, an allele in the promoter region of the human tissue kallikrein gene can be identified as an allele correlated with an increased risk of developing essential hypertension through molecular biology protocols which measure the activity of the promoter of the human tissue kallikrein gene with various alleles. For example, as described in the Examples section herein, different alleles can be identified and cloned into vectors and positioned to control the transcription of a reporter gene such as, for example, luciferase, although any reporter gene known in the art would be suitable. The amount of reporter gene product produced can be quantitated as described herein to measure the activity of a particular allele in the promoter region of the human tissue kallikrein gene. The activity of the promoter can also be determined by other protocols available in the art for measuring gene activity, including, for example, the chloramphenicol acetyltransferase assay (Sambrook et al., 1984) and the green fluorescent protein assay (GIBCO BRL Products and Reference Guide, Life Technologies, Gaithersburg, Md., 1997).

A promoter with a particular allele having less activity than a promoter with the nucleotide sequence of allele A (SEQ ID NO:14) or the nucleotide sequence of allele B (SEQ ID NO:15) identifies an allele correlated with an increased risk of developing essential hypertension. For example, an allele correlated with an increased risk of developing essential hypertension can be, but is not limited to, allele D (SEQ ID NO:17) or allele H (SEQ ID NO:20). Using data similar to that obtained for alleles D and H, other alleles can also be correlated with an increased risk of developing essential hypertension.

The amount of activity which is less than the amount of activity of a promoter containing the reference nucleotide sequence of allele A (SEQ ID NO:14) or the reference nucleotide sequence of allele B (SEQ ID NO:15) can be, for example, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50% less or greater than 50% less than the reference sequence activity. The amount of activity which is less than the reference sequence activity can also be in a range of, for example, between 1% and 10% less, between 11% and 49% less and 50% less or greater than 50% less than the reference sequence activity.

Essential hypertension is considered to be a quantitative disorder and is generally characterized in terms of marginal, moderate or severe hypertension. For example, marginal essential hypertension can be generally defined by a systolic blood pressure value greater than 120 mmHg, up to about 140 mmHg and diastolic blood pressure value greater than 90, up to about 100 mmHg. Moderate essential hypertension can be generally defined by a systolic blood pressure greater than 140 mmHg, up to about 180 mmHg and a diastolic blood pressure value greater than 100 mmHg, up to about 120 mmHg. Severe essential hypertension can be generally defined by a systolic blood pressure value greater than 180 mmHg and a diastolic blood pressure value greater than 120 mmHg. These values do not define the absolute limits for the classification of essential hypertension as marginal, moderate or severe and can vary up to ±5 mmHg for each value. It is also contemplated in the present invention that a positive correlation can exist between the percent decrease in promoter activity as compared to alleles A and B and the classification of the hypertension as marginal, moderate or severe.

The data provided herein describe promoter activity in human kidney 293 cells (ATCC CRL 1573). However, the present invention contemplates the use of any human cells which express the tissue kallikrein gene, such as any human pancreatic, kidney, prostate and salivary gland cell lines. Cells from other species which express the tissue kallikrein gene (e.g., mouse, rat) can be also be used in the present invention. For example, the cells of the present invention can be P5 human proximal kidney tubule cells (Medical University of South Carolina, Department of Biochemistry and Molecular Biology), LNCaP human prostate cells (ATCC CRL 1740), HSG human salivary gland cells (National Institute of Dental Research) and the like.

Also provided in the present invention is a method for identifying a human subject as having an increased risk of developing essential hypertension, comprising correlating the presence of a nucleic acid sequence at nucleotides −166 through −98 (Evans et al. 1989) in a human tissue kallikrein gene with an increased risk of developing essential hypertension; and determining the nucleic acid sequence of nucleotides −166 through −98 of the subject's tissue kallikrein gene, whereby a subject having a nucleic acid sequence at nucleotides −166 through −98 in the tissue kallikrein gene correlated with an increased risk of developing essential hypertension is identified as having an increased risk of developing essential hypertension.

The nucleic acid sequence of nucleotides −166 through −98 of a subject's tissue kallikrein gene can be determined, for example, as described herein, according to standard nucleic acid sequencing protocols which are well known in the art. The nucleic acid sequence of nucleotides −166 through −98 of the subject's tissue kallikrein gene can be correlated with an increased risk of developing essential hypertension on the basis of statistical analyses of the incidence of a particular nucleic acid sequence of nucleotides −166 through −98 in individuals diagnosed with essential hypertension. Furthermore, a nucleic acid sequence of nucleotides −166 through −98 can be correlated with an increased risk of developing essential hypertension on the basis of statistical analyses of the incidence of a particular nucleic acid sequence of nucleotides −166 through −98 and a decrease of the amount of urinary excretion of tissue kallikrein relative to normotensive subjects. For example, the amount of tissue kallikrein excreted in the urine by subjects who have specific nucleic acid sequences at nucleotides −166 through −98 can be determined according to methods well known in the art as described herein as well as in Shimamoto et al. (1984) and the amount of tissue kallikrein excreted in the urine by subjects diagnosed with essential hypertension can be determined as described herein. These data can be used to establish a correlation between a specific nucleic acid sequence of the nucleotides −166 through −98 in the human tissue kallikrein gene and an increased risk of developing essential hypertension.

In addition, a particular nucleic acid sequence of nucleotides −166 through −98 of the human tissue kallikrein gene can be correlated with an increased risk of developing essential hypertension as determined through molecular biology protocols which measure the activity of the promoter of the human tissue kallikrein gene with various nucleic acid sequences at nucleotides −166 through −98 of the tissue kallikrein gene. For example, as described in the Examples section herein, the promoter region of the tissue kallikrein gene with various nucleic acid sequences at nucleotides −166 through −98 can be cloned into vectors and positioned to control the transcription of a reporter gene such as, for example, luciferase. The amount of reporter gene product produced can be quantitated as described herein to measure the activity of a promoter of the human tissue kallikrein gene having a particular nucleic acid sequence at nucleotides −166 through −98.

A promoter containing a nucleic acid sequence at nucleotides −166 through −98 having less activity than a promoter containing the nucleotide sequence of allele A (SEQ ID NO:14) or the nucleotide sequence of allele B (SEQ ID NO:15) identifies a nucleic acid sequence at nucleotides −166 through −98 correlated with an increased risk of developing essential hypertension. As described above, the percent decrease in activity demonstrated by a particular nucleic acid sequence at nucleotides −166 through −98 is directly correlated with an increased risk of developing a particular degree (i.e., marginal, moderate or severe) of essential hypertension For example, as set forth above, nucleic acid sequence at nucleotides −166 through −98 correlated with an increased risk of developing severe essential hypertension can be, but is not limited to, the nucleic acid sequences at nucleotides −166 through −98 comprising allele D (SEQ ID NO:17) or comprising allele H (SEQ ID NO:20).

In addition, a method of identifying an allele in the promoter region of the human tissue kallikrein gene correlated with an increased risk of developing essential hypertension is provided. The method comprises determining the nucleic acid sequence of the nucleotides at positions −166 through −98 in the human tissue kallikrein gene from a subject; and correlating the presence of the nucleic acid sequence of the nucleotides at positions −166 through −98 of the subject with the presence of essential hypertension in the subject, whereby the nucleic acid sequence of the nucleotides at positions −166 through −98 in the promoter region of the human tissue kallikrein gene identifies an allele correlated with an increased risk of developing essential hypertension. The methods for correlating the presence of a particular nucleic acid sequence at nucleotides −98 through −166 are as described herein.

An additional method of identifying an allele in the promoter region of a human tissue kallikrein gene correlated with an increased risk of developing essential hypertension is also provided. The method comprises determining the nucleic acid sequence of the nucleotides at positions −166 through −98 in the promoter region of the human tissue kallikrein gene; cloning the nucleic acid sequence of the nucleotides at positions −166 through −98 in the promoter region of the human tissue kallikrein gene into an expression vector having a reporter gene; expressing the reporter gene to produce a gene product under the direction of the promoter region of the human tissue kallikrein gene; and determining the amount of reporter gene product produced, an amount of reporter gene product less than the amount of reporter gene product produced under the direction of a tissue kallikrein gene promoter containing a nucleic acid sequence of the nucleotides at positions −166 through −98 comprising the nucleotide sequence of SEQ ID NO:14 (allele A) or the nucleotide sequence of SEQ ID NO:15 (allele B) identifying a nucleic acid sequence of the nucleotides at position −166 through −98 of the human tissue kallikrein gene as an allele correlated with an increased risk of developing essential hypertension. As stated above, a positive correlation can exist between the percent decrease in promoter activity as compared to alleles A and B and the classification of the hypertension as marginal, moderate or severe.

The nucleic acid sequence of nucleotides −98 through −166 can be obtained according to standard nucleic acid sequencing protocols standard in the art, as described herein, for example. Cloning and expression of a reporter gene under the control of a tissue kallikrein gene promoter having various nucleic acid sequences at nucleotides −98 through −166 can also be carried out, for example, as described in the Examples herein, using molecular biology protocols for cloning and expression as are well known in the art. Measuring the amount of reporter gene product can be carried out by a variety of methods, depending on the nature of the reporter gene product. A protocol for quantitating the amount of luciferase as a reporter gene product is described in the Examples herein. Other reporter genes and methods for detection of their gene products, such as the chloramphenicol acetyltransferase assay and the green fluorescent protein assay, would be well known to the artisan and can also be employed in the present invention to measure the activity of a tissue kallikrein gene promoter having a particular nucleic acid sequence at nucleotides −98 through −166.

Furthermore, the present invention provides a method for identifying a human subject as having an increased risk of developing essential hypertension, comprising cloning the nucleic acid sequence encoding the promoter region of the human tissue kallikrein gene of the subject into an expression vector having a reporter gene; expressing the reporter gene to produce a gene product under the direction of the promoter region of the subject's human tissue kallikrein gene; and determining the amount of reporter gene product produced, an amount of reporter gene product which is less than the amount of reporter gene product produced under the direction of a tissue kallikrein gene promoter containing the nucleotide sequence of SEQ ID NO:14 (allele A) or the nucleotide sequence of SEQ ID NO:15 (allele B) identifying a subject as having an increased risk of developing essential hypertension. As stated herein, a positive correlation can exist between the percent decrease in activity relative to the activity of promoters containing alleles A or B and the classification of the hypertension as mild, moderate or severe.

In this embodiment, the exact nucleic acid sequence of the subject need not be known. The promoter region of the subject's kallikrein gene can be cloned into a vector containing a reporter gene according to standard protocols as described herein. The reporter gene product can be produced and quantitated as described herein to determine the amount of activity of the subject's kallikrein gene promoter.

The present invention also provides a method for identifying an allele in the promoter region of the human tissue kallikrein gene, comprising determining the nucleic acid sequence of the nucleotides at positions −166 through −98 of the human tissue kallikrein gene. The kallikrein gene can be isolated and the promoter region sequenced according to well defined molecular biology protocols, for example, as described herein. The present invention provides alleles A, B, C, D, E, F, G H, I, J, K, M, P and R as described in Table 1. These 14 alleles were detected in a GC-rich region between −133 bp and −121 bp upstream to the transcription initiation site in Caucasians, African-Americans and Asians. Thus, the present invention further provides isolated nucleic acids consisting of the nucleotide sequences of SEQ ID NO:14 (allele A), SEQ ID NO:15 (allele B), SEQ ID NO:16 (allele C), SEQ ID NO:17 (allele D), SEQ ID NO:18 (allele E), SEQ ID NO:19 (allele F), SEQ ID NO:20 (allele H), SEQ ID NO:21 (allele I), SEQ ID NO:22 (allele K), SEQ ID NO:23 (allele P), SEQ ID NO:24 (allele G), SEQ ID NO:25 (allele J), SEQ ID NO:26 (allele M), SEQ ID NO:27 (allele R) and SEQ ID NO:28 (allele Q). By "isolated" is meant separated from other nucleic acids found in the naturally occurring organism. Additional alleles can be identified according to the protocols set forth herein.

The present invention further provides an isolated nucleic acid consisting of the promoter region of the human tissue kallikrein gene between nucleotides −1 to −940 (Evans et al. 1988). The promoter region of the human tissue kallikrein gene has been defined as that region of the gene upstream of the coding region which confers activity to the gene. By the methods described herein for measuring promoter activity, a region of the tissue kallikrein gene which imparts activity to the gene resides in the nucleic acid sequence between nucleotides −1 to −940. Examples of these nucleic acids include those comprising alleles A, B, C, D, E, F, H, I, K, P, G, J, M, R and Q.

In addition, an isolated nucleic acid comprising the nucleic acid sequence of the primer designated hKPMA (5'-ATTCTGGGGATCGGAGGG-3') (SEQ ID NO:9) and an isolated nucleic acid comprising the nucleic acid of the primer designated hKPMB (5'-TCTGGGGATCGGAGGC-3') (SEQ ID NO:10), are provided. The isolated nucleic acid comprising the nucleotide sequence of SEQ ID NO:9 or SEQ ID NO:10 can range in size from 16 (SEQ ID NO:10) or 18 nucleotides (SEQ ID NO:9), respectively, to an upper limit of about 940 nucleotides, including any number of nucleotides in that range. By "isolated" is meant separated from other nucleic acids found in the naturally occurring organism. These nucleic acids can be used as forward primers in an allele specific amplification (ASA) method to identify the presence or absence of the two most frequently occurring alleles, A or B, in a subject, as described herein. These primer sequences are specific for the A and B alleles, respectively and can be employed in a PCR protocol optimized as described in the Examples herein to distinguish alleles A and B from other alleles on the basis of a variation at a single nucleotide in the promoter region of the tissue kallikrein gene.

In another embodiment, the present invention provides a method of identifying a subject as having a reduced risk of developing essential hypertension, comprising determining the presence in the subject of an allele in the promoter region of the subject's tissue kallikrein gene correlated with a reduced risk of developing essential hypertension, the presence of the allele identifying the subject as having a reduced risk of developing essential hypertension. The presence of an allele correlated with a reduced risk of developing essential hypertension is determined by isolating the promoter region of the subject's tissue kallikrein gene and determining the nucleic acid sequence of the promoter according to standard molecular biology protocols well known in the art as described for example in Sambrook et al. (1989) and as set forth in the Examples provided herein.

An allele in the promoter region of the human tissue kallikrein gene can be identified as correlated with a reduced risk of developing essential hypertension on the basis of statistical analyses of the incidence of a particular allele in individuals without essential hypertension according to the 2-tailed t test, which is well known in the art. Furthermore, an allele in the promoter region of the human kallikrein gene can be identified as an allele correlated with a reduced risk of developing essential hypertension on the basis of statistical analyses of the incidence of a particular allele in individuals demonstrating an increased amount of urinary excretion of tissue kallikrein, relative to the average amount of urinary excretion of tissue kallikrein as determined for a large number of normotensive individuals. For example, the amount of tissue kallikrein excreted in the urine by subjects who have specific alleles can be determined according to method well known in the art as described herein as well as in Shimamoto et al. (1984) and the amount of tissue kallikrein excreted in the urine by subjects who do not have essential hypertension can be determined as described herein. These data can be used to establish a correlation between a specific allele in the promoter region of the human tissue kallikrein gene and a reduced risk of developing essential hypertension. For example, allele K has been found to be correlated with an increased amount of urinary tissue kallikrein excretion relative to average amounts excreted by normotensive individuals. Therefore, an allele of the present invention correlated with a reduced risk of developing essential hypertension can be, but is not limited to, allele K (SEQ ID NO:22).

In addition, an allele in the promoter region of the human tissue kallikrein gene can be identified as an allele correlated with a reduced risk of developing essential hypertension as determined through molecular biology protocols which measure the activity of the promoter of the human tissue kallikrein gene with various alleles. For example, as described in the Examples section herein, different alleles can be cloned into vectors and positioned to control the transcription of a reporter gene such as, for example, luciferase. The amount of reporter gene product produced can be quantitated as described herein to measure the activity of a particular allele in the promoter region of the human tissue kallikrein gene. A promoter containing an allele having more activity than a promoter containing allele A (SEQ ID NO:14) or a promoter containing allele B (SEQ ID NO:15) identifies an allele correlated with a reduced risk of developing essential hypertension.

Additionally, the present invention provides a method for identifying a human subject as having a reduced risk of developing essential hypertension comprising correlating the presence of a nucleic acid sequence at nucleotides −166 through −98 in a human tissue kallikrein gene with a reduced risk of developing essential hypertension; and determining the nucleic acid sequence of nucleotides −166 through −98 of the subject's tissue kallikrein gene, whereby a subject having a nucleic acid sequence at nucleotides −166 through −98 in the tissue kallikrein gene correlated with a reduced risk of developing essential hypertension is identified as having a reduced risk of developing essential hypertension.

The nucleic acid sequence of nucleotides −166 through −98 of a subject's tissue kallikrein gene can be determined, for example as described herein, according to standard nucleic acid sequencing protocols which are well known in the art. The nucleic acid sequence of nucleotides −166 through −98 of the subject's tissue kallikrein gene can be correlated with a reduced risk of developing essential hypertension on the basis of statistical analyses of the incidence of a particular nucleic acid sequence of nucleotides −166 through −98 in individuals who are normotensive, i.e., who do not have essential hypertension. Furthermore, a nucleic acid sequence of nucleotides −166 through −98 can be correlated with a reduced risk of developing essential hypertension on the basis of statistical analyses of the incidence of a particular nucleic acid sequence of nucleotides −166 through −98 with an increase in the amount of urinary excretion of tissue kallikrein in a subject relative to the average amount of urinary tissue kallikrein excreted by normotensive individuals. For example, the amount of tissue kallikrein excreted in the urine by subjects who have specific nucleic acid sequences at nucleotides −166 through −98 can be determined according to methods well known in the art as described herein as well as in Shimamoto et al. (1984) and the amount of tissue kallikrein excreted in the urine by subjects who are normotensive can be determined as described herein and the data provided can be used to establish a correlation between a specific nucleic acid sequence of the nucleotides −166 through −98 in the human tissue kallikrein gene and a reduced risk of developing essential hypertension.

In addition, a particular nucleic acid sequence of nucleotides −166 through −98 of the human tissue kallikrein gene can be correlated with a reduced risk of developing essential hypertension as determined through molecular biology protocols which measure the activity of the promoter of the human tissue kallikrein gene with various nucleic acid sequences at nucleotides −166 through −98 of the tissue kallikrein gene. For example, as described in the Examples section herein, the promoter region of the tissue kallikrein gene with various nucleic acid sequences at nucleotides −166 through −98 can be cloned into vectors and positioned to control the transcription of a reporter gene such as, for example, luciferase. The amount of reporter gene product produced can be quantitated as described herein to measure the activity of a promoter of the human tissue kallikrein gene having a particular nucleic acid sequence at nucleotides −166 through −98. A promoter containing a nucleic acid sequence at nucleotides −166 through −98 having more activity than a promoter containing the nucleotide sequence of allele A (SEQ ID NO:14) or the nucleotide sequence of allele B (SEQ ID NO:15) identifies a nucleic acid sequence at nucleotides −166 through −98 correlated with a reduced risk of developing essential hypertension.

A method of identifying an allele in the promoter region of the human tissue kallikrein gene correlated with a reduced risk of developing essential hypertension is provided herein as well, comprising determining the nucleic acid sequence of the nucleotides at positions −166 through −98 in the human tissue kallikrein gene from a subject; and correlating the presence of the nucleic acid sequence of the subject with the lack of essential hypertension in the subject, whereby the nucleic acid sequence of the nucleotides at positions −166 through −98 in the promoter region of the human tissue kallikrein gene identifies an allele correlated with a reduced risk of developing essential hypertension. The methods for correlating the presence of a particular nucleic acid sequence at nucleotides −98 through −166 with a reduced risk of developing essential hypertension are as described herein.

Also provided is a method of identifying an allele in the promoter region of a human tissue kallikrein gene correlated with a reduced risk of developing essential hypertension, comprising determining the nucleic acid sequence of the nucleotides at positions −166 through −98 in the promoter region of the human tissue kallikrein gene; cloning the nucleic acid sequence encoding the promoter region of the human tissue kallikrein gene into an expression vector having a reporter gene; expressing the reporter gene to produce a gene product under the direction of the promoter region of the human tissue kallikrein gene; and determining the amount of reporter gene product produced, an amount of reporter gene product more than the amount of reporter gene product produced under the direction of a tissue kallikrein gene promoter containing a nucleic acid sequence of the nucleotides at positions −166 through −98 comprising the nucleotide sequence of SEQ ID NO:14 (allele A) or the nucleotide sequence of SEQ ID NO:15 (allele B) identifying a nucleic acid sequence of the nucleotides at position −166 through −98 of the human tissue kallikrein gene as correlated with a reduced risk of developing essential hypertension.

The nucleic acid sequence of nucleotides −98 through −166 can be obtained according to standard nucleic acid sequencing protocols standard in the art, as described herein, for example. Cloning and expression of a reporter gene under the control of a tissue kallikrein gene promoter having various nucleic acid sequences at nucleotides −98 through −166 can also be carried out, for example, as described in the Examples herein, using molecular biology protocols for cloning and expression as are well known in the art. Measuring the amount of reporter gene product can be carried out by a variety of methods, depending on the nature of the reporter gene product. A protocol for quantitating the amount of luciferase as a reporter gene product is described in the Examples herein. Other reporter genes and methods for detection of their gene products would be well known to the artisan and can also be employed in the present invention to measure the activity of a tissue kallikrein gene promoter having a particular nucleic acid sequence at nucleotides −98 through −166.

Furthermore, the present invention provides a method for identifying a human subject as having a reduced risk of developing essential hypertension comprising cloning the nucleic acid sequence encoding the promoter region of the human tissue kallikrein gene of the subject into an expression vector having a reporter gene; expressing the reporter gene to produce a gene product under the direction of the promoter region of the subject's human tissue kallikrein gene; and determining the amount of reporter gene product produced, an amount of reporter gene product greater than the amount of reporter gene product produced under the direction of a tissue kallikrein gene promoter containing the nucleotide sequence of SEQ ID NO:14 (allele A) or the nucleotide sequence of SEQ ID NO:15 (allele B) identifying a subject as having a reduced risk of developing essential hypertension.

In this embodiment, the exact nucleic acid sequence of the subject need not be known. The promoter region of the subject's kallikrein gene can be cloned into a vector containing a reporter gene according to standard protocols as described herein. The reporter gene product can be produced and quantitated as described herein to determine the amount of activity of the subject's kallikrein gene promoter. A subject determined to have a promoter with greater activity than promoters containing the nucleotide sequences of alleles A and B is identified as a subject having a reduced risk of developing essential hypertension.

It is further contemplated that the present invention provides a method for identifying a human subject as having an increased likelihood of regulating blood pressure with dietary sodium intake, comprising determining the presence in the subject of a tissue kallikrein promoter allele genotype correlated with an increased likelihood of regulating blood pressure with dietary sodium intake, whereby the presence of the genotype identifies the subject as having an increased likelihood of regulating blood pressure with dietary sodium intake.

Genotyping of a subject is done by identifying the particular alleles present in the promoter region of the subject's tissue kallikrein genes. The identification of an allele is determined by isolating the promoter region of the subject's tissue kallikrein gene and determining the nucleic acid sequence of the promoter according to standard molecular biology protocols well known in the art as described for example in Sambrook et al. (1989) and as set forth in the Examples provided herein. The nucleic acid sequence of several examples of the alleles of the present invention are set forth in Table 1.

A tissue kallikrein promoter allele genotype can be identified as correlated with an increased likelihood of regulating blood pressure with dietary sodium intake on the basis of statistical analyses of the identification of a particular genotype in individuals who exhibit a reduction in blood pressure under conditions of low sodium intake according to the 2-tailed t test, which is well known in the art. Furthermore, a tissue kallikrein promoter genotype can be identified as a genotype correlated with an increased likelihood of regulating blood pressure with dietary sodium intake on the basis of statistical analyses of the incidence of a particular genotype in individuals demonstrating an increase in the amount of urinary excretion of tissue kallikrein with low dietary sodium intake as compared to normal or unrestricted dietary sodium intake. For example, the amount of tissue kallikrein excreted in the urine by subjects who have a specific genotype can be determined according to methods well known in the art as described herein as well as in, for example, Shimamoto et al (1984). The amount of tissue kallikrein excreted in the urine by these subjects on a low sodium diet and on a normal sodium diet can be determined as described herein and subjects who demonstrate an increase in urinary kallikrein excretion in response to low sodium intake can be identified. These data can be used to establish a correlation between a specific genotype and an increase in urinary kallikrein in response to low sodium intake, thereby establishing a correlation between genotype and an increased likelihood of regulating blood pressure with dietary sodium intake (phenotype).

In addition, the present invention provides a method of identifying a human subject as having an increased likelihood of regulating blood pressure with dietary sodium intake, comprising a) correlating the presence of tissue kallikrein promoter allele genotype with an increased likelihood of regulating blood pressure with dietary sodium intake; and b) determining the tissue kallikrein promoter allele genotype of the subject, whereby a subject having a tissue kallikrein promoter allele genotype correlated with an increased likelihood of regulating blood pressure with dietary sodium intake is identified as having an increased likelihood of regulating blood pressure with dietary sodium intake.

Furthermore, a method is provided herein of identifying a tissue kallikrein promoter genotype correlated with an increased likelihood of regulating blood pressure with dietary sodium intake, comprising a) determining the tissue kallikrein promoter allele genotype; and b) correlating the genotype of step (a) with the ability of the subject to regulate blood pressure by dietary sodium intake, thereby identifying a genotype correlated with an increased likelihood of regulating blood pressure by dietary sodium intake.

To determine the tissue kallikrein promoter allele genotype, the nucleic acid sequence of nucleotides −166 through −98 of a subject's tissue kallikrein genes can be determined, for example, as described herein, according to standard nucleic acid sequencing protocols which are well known in the art. The nucleic acid sequence of nucleotides −166 through −98 of the subject's tissue kallikrein genes can be used to identify the tissue kallikrein promoter alleles of the subject and thus, the genotype of the subject. The subject's genotype can be correlated with an increased likelihood of regulating blood pressure with dietary sodium intake on the basis of statistical analyses of the incidence of a particular genotype in individuals and blood pressure reduction or an increase in urinary kallikrein excretion under conditions of low sodium intake, as described herein.

Additionally, the present invention provides a method for identifying a human subject as having a reduced likelihood of regulating blood pressure with dietary sodium intake, comprising determining the presence in the subject of tissue kallikrein promoter allele genotype correlated with a reduced likelihood of regulating blood pressure with dietary sodium intake, whereby the presence of the genotype identifies the subject as having a reduced likelihood of regulating blood pressure with dietary sodium intake.

A tissue kallikrein promoter allele genotype can be identified as correlated with a reduced likelihood of regulating blood pressure with dietary sodium intake on the basis of statistical analyses of the identification of a particular genotype in individuals who do not exhibit a significant reduction in blood pressure under conditions of low sodium intake according to the 2-tailed t test, which is well known in the art. For example, genotype A/K has been determined, according to the methods of this invention, to be a genotype correlated with a reduced likelihood of regulating blood pressure with dietary sodium intake.

Furthermore, a tissue kallikrein promoter genotype can be identified as a genotype correlated with a reduced likelihood of regulating blood pressure with dietary sodium intake on the basis of statistical analyses of the incidence of a particular genotype in individuals demonstrating a decrease or no significant change in the amount of urinary excretion of tissue kallikrein with low dietary sodium intake as compared to normal or unrestricted dietary sodium intake. For example, the amount of tissue kallikrein excreted in the urine by subjects who have a specific genotype can be determined according to methods well known in the art as described herein as well as in, for example, Shimamoto et al (1984). The amount of tissue kallikrein excreted in the urine by these subjects on a low sodium diet and on a normal sodium diet can be determined as described herein and subjects who demonstrate a decrease or no change in urinary kallikrein excretion in response to low sodium intake can be identified. These data can be used to establish a correlation between a specific genotype and a decrease or no change in urinary kallikrein excretion in response to low sodium intake and therefore, establish a correlation between a genotype and a reduced likelihood of regulating blood pressure with dietary sodium intake (phenotype).

In addition, the present invention provides a method of identifying a human subject as having a reduced likelihood of regulating blood pressure with dietary sodium intake, comprising a) correlating the presence of a tissue kallikrein promoter allele genotype with a reduced likelihood of regulating blood pressure with dietary sodium intake; and b) determining the tissue kallikrein promoter allele genotype of a subject, whereby a subject having a tissue kallikrein promoter allele genotype correlated with a reduced likelihood of regulating blood pressure with dietary sodium intake is identified as having a reduced likelihood of regulating blood pressure with dietary sodium intake.

A method is additionally provided herein of identifying a tissue kallikrein promoter genotype correlated with a reduced likelihood of regulating blood pressure with dietary sodium intake, comprising a) determining the tissue kallikrein promoter allele genotype of a subject; and b) correlating the genotype of step (a) with the ability of the subject to regulate blood pressure by dietary sodium intake, thereby identifying a tissue kallikrein promoter allele genotype correlated with a reduced likelihood of regulating blood pressure by dietary sodium intake.

To determine the tissue kallikrein promoter allele genotype, the nucleic acid sequence of nucleotides −166 through −98 of a subject's tissue kallikrein genes can be determined, for example, as described herein, according to standard nucleic acid sequencing protocols which are well known in the art. The nucleic acid sequence of nucleotides −166 through −98 of the subject's tissue kallikrein genes can be used to identify the tissue kallikrein promoter alleles of the subject and thus the subject's genotype. The subject's genotype can by correlated with a reduced likelihood of regulating blood pressure with dietary sodium intake on the basis of statistical analyses of the incidence of a particular genotype in individuals and a lack of blood pressure reduction, or a decrease or no change in urinary kallikrein excretion in these individuals under conditions of low sodium intake, as described herein.

It is further contemplated that the present invention provides a method for identifying a human subject as having an increased likelihood of regulating blood pressure with a diuretic, comprising determining the presence in the subject of a tissue kallikrein promoter allele genotype correlated with an increased likelihood of regulating blood pressure with a diuretic, whereby the presence of the genotype identifies the subject as having an increased likelihood of regulating blood pressure with a diuretic.

Genotyping of a subject is done by identifying the particular alleles present in the promoter region of the subject's tissue kallikrein genes. The identification of an allele is determined by isolating the promoter region of the subject's tissue kallikrein gene and determining the nucleic acid sequence of the promoter according to standard molecular biology protocols well known in the art as described for example in Sambrook et al. (1989) and as set forth in the Examples provided herein. The nucleic acid sequence of several examples of the alleles of the present invention are set forth in Table 1.

A tissue kallikrein promoter allele genotype can be identified as correlated with an increased likelihood of regulating blood pressure with a diuretic on the basis of statistical analyses of the identification of a particular genotype in individuals who exhibit a reduction in blood pressure in response to a diuretic, according to the 2-tailed t test, which is well known in the art. Furthermore, a tissue kallikrein promoter genotype can be identified as a genotype correlated with an increased likelihood of regulating blood pressure with a diuretic on the basis of statistical analyses of the incidence of a particular genotype in individuals demonstrating an increase in the amount of urinary excretion of tissue kallikrein in response to a diuretic, as compared to the amount of urinary excretion of tissue kallikrein in the absence of a diuretic. For example, the amount of tissue kallikrein excreted in the urine by subjects who have a specific genotype can be determined according to methods well known in the art as described herein as well as in, for example, Shimamoto et al (1984). The amount of tissue kallikrein excreted in the urine by these subjects with and without a diuretic can be determined as described herein and subjects who demonstrate an increase in urinary kallikrein excretion in response to the diuretic can be identified. These data can be used to establish a correlation between a specific genotype and an increase in urinary kallikrein in response to a diuretic, thereby establishing a correlation between genotype and an increased likelihood of regulating blood pressure with a diuretic (phenotype).

In addition, the present invention provides a method of identifying a human subject as having an increased likelihood of regulating blood pressure with a diuretic, comprising a) correlating the presence of tissue kallikrein promoter allele genotype with an increased likelihood of regulating blood pressure with a diuretic; and b) determining the tissue kallikrein promoter allele genotype of the subject, whereby a subject having a tissue kallikrein promoter allele genotype correlated with an increased likelihood of regulating blood pressure with a diuretic is identified as having an increased likelihood of regulating blood pressure with a diuretic.

Furthermore, a method is provided herein of identifying a tissue kallikrein promoter genotype correlated with an increased likelihood of regulating blood pressure with a diuretic, comprising a) determining the tissue kallikrein promoter allele genotype; and b) correlating the genotype of step (a) with the ability of the subject to regulate blood pressure with a diuretic, thereby identifying a genotype correlated with an increased likelihood of regulating blood pressure with a diuretic.

To determine the tissue kallikrein promoter allele genotype, the nucleic acid sequence of nucleotides −166 through −98 of a subject's tissue kallikrein genes can be determined, for example, as described herein, according to standard nucleic acid sequencing protocols which are well known in the art. The nucleic acid sequence of nucleotides −166 through −98 of the subject's tissue kallikrein genes can be used to identify the tissue kallikrein promoter alleles of the subject and thus, the genotype of the subject. The subject's genotype can be correlated with an increased likelihood of regulating blood pressure with a diuretic on the basis of statistical analyses of the incidence of a particular genotype in individuals and blood pressure reduction or an increase in urinary kallikrein excretion in response to a diuretic, as described herein.

Additionally, the present invention provides a method for identifying a human subject as having a reduced likelihood of regulating blood pressure with a diuretic, comprising determining the presence in the subject of tissue kallikrein promoter allele genotype correlated with a reduced likelihood of regulating blood pressure with a diuretic, whereby the presence of the genotype identifies the subject as having a reduced likelihood of regulating blood pressure with a diuretic.

A tissue kallikrein promoter allele genotype can be identified as correlated with a reduced likelihood of regulating blood pressure with a diuretic on the basis of statistical analyses of the identification of a particular genotype in individuals who do not exhibit a significant reduction in blood pressure in response to a diuretic, according to the 2-tailed t test, which is well known in the art.

Furthermore, a tissue kallikrein promoter genotype can be identified as a genotype correlated with a reduced likelihood of regulating blood pressure with a diuretic on the basis of statistical analyses of the incidence of a particular genotype in individuals demonstrating a decrease or no significant change in the amount of urinary excretion of tissue kallikrein in response to a diuretic as compared to the amount of urinary excretion of tissue kallikrein without a diuretic. For example, the amount of tissue kallikrein excreted in the urine by subjects who have a specific genotype can be determined according to methods well known in the art as described herein as well as in, for example, Shimamoto et al (1984). The amount of tissue kallikrein excreted in the urine by these subjects with and without a diuretic can be determined as described herein and subjects who demonstrate a decrease or no change in urinary kallikrein excretion in response to a diuretic can be identified. These data can be used to establish a correlation between a specific genotype and a decrease or no change in urinary kallikrein excretion in response to a diuretic and therefore, establish a correlation between a genotype and a reduced likelihood of regulating blood pressure with a diuretic (phenotype).

In addition, the present invention provides a method of identifying a human subject as having a reduced likelihood of regulating blood pressure with a diuretic, comprising a) correlating the presence of a tissue kallikrein promoter allele genotype with a reduced likelihood of regulating blood pressure with a diuretic; and b) determining the tissue kallikrein promoter allele genotype of a subject, whereby a subject having a tissue kallikrein promoter allele genotype correlated with a reduced likelihood of regulating blood pressure with a diuretic is identified as having a reduced likelihood of regulating blood pressure with a diuretic.

A method is additionally provided herein of identifying a tissue kallikrein promoter genotype correlated with a reduced likelihood of regulating blood pressure with a diuretic comprising a) determining the tissue kallikrein promoter allele genotype of a subject; and b) correlating the genotype of step (a) with the ability of the subject to regulate blood pressure with a diuretic, thereby identifying a tissue kallikrein promoter allele genotype correlated with a reduced likelihood of regulating blood pressure with a diuretic.

To determine the tissue kallikrein promoter allele genotype, the nucleic acid sequence of nucleotides −166 through −98 of a subject's tissue kallikrein genes can be determined, for example, as described herein, according to standard nucleic acid sequencing protocols which are well known in the art. The nucleic acid sequence of nucleotides −166 through −98 of the subject's tissue kallikrein genes can be used to identify the tissue kallikrein promoter alleles of the subject and thus the subject's genotype. The subject's genotype can by correlated with a reduced likelihood of regulating blood pressure with a diuretic on the basis of statistical analyses of the incidence of a particular genotype in individuals and a lack of blood pressure reduction, or a decrease or no change in urinary kallikrein excretion in these individuals in response to a diuretic, as described herein.

It is further contemplated that the present invention provides a method for identifying a human subject as having an increased likelihood of regulating blood pressure with an ACE inhibitor, comprising determining the presence in the subject of a tissue kallikrein promoter allele genotype correlated with an increased likelihood of regulating blood pressure with an ACE inhibitor, whereby the presence of the genotype identifies the subject as having an increased likelihood of regulating blood pressure with an ACE inhibitor.

Genotyping of a subject is done by identifying the particular alleles present in the promoter region of the subject's tissue kallikrein genes. The identification of an allele is determined by isolating the promoter region of the subject's tissue kallikrein gene and determining the nucleic acid sequence of the promoter according to standard molecular biology protocols well known in the art as described for example in Sambrook et al. (1989) and as set forth in the Examples provided herein. The nucleic acid sequence of several examples of the alleles of the present invention are set forth in Table 1.

A tissue kallikrein promoter allele genotype can be identified as correlated with an increased likelihood of regulating blood pressure with an ACE inhibitor on the basis of statistical analyses of the identification of a particular genotype in individuals who exhibit a reduction in blood pressure in response to an ACE inhibitor, according to the 2-tailed t test, which is well known in the art. Furthermore, a tissue kallikrein promoter genotype can be identified as a genotype correlated with an increased likelihood of regulating blood pressure with an ACE inhibitor on the basis of statistical analyses of the incidence of a particular genotype in individuals demonstrating an increase in the amount of urinary excretion of tissue kallikrein in response to an ACE inhibitor, as compared to the amount of urinary excretion of tissue kallikrein without an ACE inhibitor. For example, the amount of tissue kallikrein excreted in the urine by subjects who have a specific genotype can be determined according to methods well known in the art as described herein as well as in, for example, Shimamoto et al (1984). The amount of tissue kallikrein excreted in the urine by these subjects with and without an ACE inhibitor can be determined as described herein and subjects who demonstrate an increase in urinary kallikrein excretion in response to an ACE inhibitor can be identified. These data can be used to establish a correlation between a specific genotype and an increase in urinary kallikrein in response to an ACE inhibitor, thereby establishing a correlation between genotype and an increased likelihood of regulating blood pressure with an ACE inhibitor (phenotype).

In addition, the present invention provides a method of identifying a human subject as having an increased likelihood of regulating blood pressure with an ACE inhibitor, comprising a) correlating the presence of tissue kallikrein promoter allele genotype with an increased likelihood of regulating blood pressure with an ACE inhibitor; and b) determining the tissue kallikrein promoter allele genotype of the subject, whereby a subject having a tissue kallikrein promoter allele genotype correlated with an increased likelihood of regulating blood pressure with an ACE inhibitor is identified as having an increased likelihood of regulating blood pressure with an ACE inhibitor.

Furthermore, a method is provided herein of identifying a tissue kallikrein promoter genotype correlated with an increased likelihood of regulating blood pressure with an ACE inhibitor, comprising a) determining the tissue kallikrein promoter allele genotype of a subject; and b) correlating the genotype of step (a) with the ability of the subject to regulate blood pressure with an ACE inhibitor, thereby identifying a genotype correlated with an increased likelihood of regulating blood pressure with an ACE inhibitor.

To determine the tissue kallikrein promoter allele genotype, the nucleic acid sequence of nucleotides −166 through −98 of a subject's tissue kallikrein genes can be determined, for example, as described herein, according to standard nucleic acid sequencing protocols which are well known in the art. The nucleic acid sequence of nucleotides −166 through −98 of the subject's tissue kallikrein genes can be used to identify the tissue kallikrein promoter alleles of the subject and thus, the genotype of the subject. The subject's genotype can be correlated with an increased likelihood of regulating blood pressure with an ACE inhibitor on the basis of statistical analyses of the incidence of a particular genotype in individuals and blood pressure reduction or an increase in urinary kallikrein excretion in response to an ACE inhibitor, as described herein.

Additionally, the present invention provides a method for identifying a human subject as having a reduced likelihood of regulating blood pressure with an ACE inhibitor, comprising determining the presence in the subject of tissue kallikrein promoter allele genotype correlated with a reduced likelihood of regulating blood pressure with an ACE inhibitor, whereby the presence of the genotype identifies the subject as having a reduced likelihood of regulating blood pressure with an ACE inhibitor.

A tissue kallikrein promoter allele genotype can be identified as correlated with a reduced likelihood of regulating blood pressure with an ACE inhibitor on the basis of statistical analyses of the identification of a particular genotype in individuals who do not exhibit a significant reduction in blood pressure in response to an ACE inhibitor, according to the 2-tailed t test, which is well known in the art.

Furthermore, a tissue kallikrein promoter genotype can be identified as a genotype correlated with a reduced likelihood of regulating blood pressure with an ACE inhibitor on the basis of statistical analyses of the incidence of a particular genotype in individuals demonstrating a decrease or no significant change in the amount of urinary excretion of tissue kallikrein in response to an ACE inhibitor. For example, the amount of tissue kallikrein excreted in the urine by subjects who have a specific genotype can be determined according to methods well known in the art as described herein as well as in, for example, Shimamoto et al (1984). The amount of tissue kallikrein excreted in the urine by these subjects in response to an ACE inhibitor can be determined as described herein and subjects who demonstrate a decrease or no change in urinary kallikrein excretion in response to the ACE inhibitor can be identified. These data can be used to establish a correlation between a specific genotype and a decrease or no change in urinary kallikrein excretion in response to an ACE inhibitor and therefore, establish a correlation between a genotype and a reduced likelihood of regulating blood pressure with an ACE inhibitor (phenotype).

In addition, the present invention provides a method of identifying a human subject as having a reduced likelihood of regulating blood pressure with an ACE inhibitor, comprising a) correlating the presence of a tissue kallikrein promoter allele genotype with a reduced likelihood of regulating blood pressure with an ACE inhibitor; and b) determining the tissue kallikrein promoter allele genotype of a subject, whereby a subject having a tissue kallikrein promoter allele genotype correlated with a reduced likelihood of regulating blood pressure with an ACE inhibitor is identified as having a reduced likelihood of regulating blood pressure with an ACE inhibitor.

A method is additionally provided herein of identifying a tissue kallikrein promoter genotype correlated with a reduced likelihood of regulating blood pressure with an ACE inhibitor comprising a) determining the tissue kallikrein promoter allele genotype of a subject; and b) correlating the genotype of step (a) with the ability of the subject to regulate blood pressure with an ACE inhibitor, thereby identifying a tissue kallikrein promoter allele genotype correlated with a reduced likelihood of regulating blood pressure with an ACE inhibitor.

To determine the tissue kallikrein promoter allele genotype, the nucleic acid sequence of nucleotides −166 through −98 of a subject's tissue kallikrein genes can be determined, for example, as described herein, according to standard nucleic acid sequencing protocols which are well known in the art. The nucleic acid sequence of nucleotides −166 through −98 of the subject's tissue kallikrein genes can be used to identify the tissue kallikrein promoter alleles of the subject and thus the subject's genotype. The subject's genotype can by correlated with a reduced likelihood of regulating blood pressure with an ACE inhibitor on the basis of statistical analyses of the incidence of a particular genotype in individuals and a lack of blood pressure reduction, or a decrease or no change in urinary kallikrein excretion in these individuals in response to an ACE inhibitor, as described herein.

As provided herein, a diuretic of this invention can be, but is not limited to, chlorothalidone (HYGROTON), hydrochlorothiazide (HYDRODIURIL; MICROZIDE; ESIDRIX), indapamide (LOZOL), metolazone (MYKROX; ZAROXOLYN), bumetanide (BUMEX), ethacrynic acid (EDECRIN), furosemide (LASIX), torsemide (DEMADEX), amiloride hydrochloride (MIDAMOR), spironolactone (ALDACTONE) and triamterene (DYRENIUM), as well as any other substance now known or later identified to be a diuretic. The use of a diuretic for the treatment of hypertension is well documented in the art and the dosage and modes of administration of a diuretic for the treatment of hypertension, as well as the clinical parameters which would be monitored to determine efficacy of treatment, would be well known to the skilled practitioner.

As also provided herein, an angiotensin converting enzyme inhibitor (ACEI) of this invention can be, but is not limited to, benazepril hydrochloride (LOTENSIN), captopril (CAPOTEN), enalapril maleate (VASOTEC), fosinopril sodium (MONOPRIL), lisinopril (PRINIVIL; ZESTRIL), moexipril (UNIVASC), quiapril hydrochloride (ACCUPRIL), ramipril (ALTACE) and trandolapril (MAVIK), as well as any other substance now known or later identified to be an ACE inhibitor. The use of an ACE inhibitor for the treatment of hypertension is well documented in the art and the dosage and modes of administration of an ACE inhibitor for the treatment of hypertension, as well as the clinical parameters which would be monitored to determine efficacy of treatment, would be well known to the skilled practitioner.

It is also contemplated that any and all of the methods of the present invention can be used to identify a subject's increased or decreased likelihood of regulating blood pressure with other anti-hypertensive drugs, such as vasodilators (e.g., hydralazine (APRESOLINE); minoxidil (LONITEN), as well as any other drug now known or later identified to have anti-hypertensive activity.

The present invention is more particularly described in the following examples which are intended as illustrative only since numerous modifications and variations therein will be apparent to those skilled in the art.

EXAMPLES

Population and preparation of genomic DNA. DNA from 108 unrelated subjects including 57 Caucasians, 33 African-Americans and 18 Asians were used for this study. Human genomic DNA was prepared from peripheral blood leukocytes as described previously (Bell et al., 1981).

Amplification of the 5' flanking region of tissue kallikrein gene and direct DNA sequencing. A 996 bp fragment of the 5' flanking region of the human tissue kallikrein gene was amplified by PCR using oligonucleotide primers hKPM1 (5'-CTGCAGGAATCTAGTTC-3') (SEQ ID NO:1) and HUKATG (5'-CAGAACCAGGAACCACAT-3') (SEQ ID NO:2) derived from the hKLK1 sequence (Evans et al., 1988). PCR was performed in a 50 µl reaction mixture containing 5 µl of 10×PCR buffer, 5 µl of 2 mM dNTP, 50 pmoles of each primer, 2.5 U of Taq DNA polymerase and 300 ng of genomic DNA. Thirty cycles of PCR were performed in a thermal cycler with a denaturing phase of 1 min at 94° C., annealing phase of 2 min at 50° C. and extension phase of 3 min at 72° C. The resulting PCR products were purified by STE Select-D G50 columns (5Prime-3Prime). An aliquot (5 µl) of the purified PCR product was used for DNA sequencing using the primers hKPM2 (5'-ATCTGGAGGCACTAGGA-3') (SEQ ID NO:3), hKPM3 (5'-TCCTAGTGCCTCCAGAT-3') (SEQ ID NO:4), hKPM4 (5'-GTACCAGGGTCACTGAT-3') (SEQ ID NO:5), hKPM5 (5'-ATCAGTGACCCTGGTAC-3') (SEQ ID NO:6), hKPM6 (5'-GAATGCGTCCAGCGTGATCC-3') (SEQ ID NO:7)and hKPM7 (5'-AGCCCTTATCCCCTCAGAGC-3') (SEQ ID NO:8). Sequencing was performed with a double-stranded DNA cycle sequencing system (BRL) following the protocol recommended by the manufacturer. The sequence of the polymorphic region was verified by sequencing the complementary strands. PCR and sequencing were repeated at least twice to eliminate the possibility of introducing mutations during PCR amplification. Oligonucleotides were synthesized by the phosphoramidite method using the ABI (Applied Biosystems) Model 380B DNA synthesizer.

Single-stranded conformation polymorphism analysis (SSCP). The primers used for SSCP were hKPM6 and hKPM7. The 5' primer hKPM6 (20 pmol) was end-labeled with [$\gamma$-$^{32}$p] (40 µCi) ATP and 10 U of T4 DNA kinase BRL) in a total volume of 20 µl at 37° C. for 30 min. The labeled hKPM6 was purified with STE Select-D G25 column (5Prime-3Prime). PCR was performed in a 25 µl reaction mixture containing 25 pmol of unlabeled primers, 1.25 pmol of labeled hKPM6, 0.2 mM dNTP, 2.5 µl of 10×PCR buffer, 100 ng genomic DNA and 2.5 U of Taq DNA polymerase. Thirty cycles of PCR (94° C./1 min, 60° C./2 min, 72° C./3 min) were performed. PCR reaction mixtures were combined with 25 µl of stop solution (95% formamide, 20 mM EDTA, 0.05% bromophenol blue and 0.05% xylene cyanol), heated at 95° C. for 5 min and put on ice. Samples of 1 µl each were applied to a 6% non-denaturing polyacrylamide gel containing 90 mM Tris-borate, 4 mM EDTA, pH 8.3 and 10% glycerol. Electrophoresis was performed at 31 W (approximately 25 V/cm) for 3 hours at room temperature with cooling using a fan. The gel was dried on filter paper and exposed to Kodak X-Omat AR film at −80° C. for 15 hours.

Allele-specific amplification (ASA). A 180 bp fragment containing the polymorphic region was amplified using hKPM6 and hKPM7 primers. The reaction was performed with 25 ng of genomic DNA in a 25 µl reaction mixture containing 25 pmol of primers, 0.2 mM dNTP, 2.5 µl of 10×PCR buffer and 2.5 U of Taq DNA polymerase using the same PCR program as for SSCP. The PCR products were diluted 1:100 with water. Two allele-specific primers were used in this experiment, hKPMA (5'-ATTCTGGGGATCGGAGGG-3') (SEQ ID NO:9) and hKPMB (5'-TCTGGGGATCGGAGGC-3') (SEQ ID NO:10). PCR was performed in a 25 µl total volume containing 20 pmol of primers (hKPM7 and either hKPMA or hKPMB), 0.2 mM dNTP, 2.5 µl of 10×PCR buffer, 2.5 U of Taq DNA polymerase and 0.2 µl of diluted PCR products from the first round amplification. Thermal cycling pattern was 94° C./1 min, 66° C./40 sec and 72° C./20 sec. After 32 cycles of PCR, the products were analyzed by electrophoresis on 2% agarose gels containing ethidium bromide and visualized by ultraviolet illumination.

Sequencing gel-based PCR analysis. The primers used in this experiment were hKPM8 (5'-

GTGATCCAGGGCCTGCA-3') (SEQ ID NO:11) and hKPM9 (5'-CTTCCCCTGTTGCCTGG-3') (SEQ ID NO:12). The 5' primer, hKPM9 (20 pmol), was end-labeled and purified as described above. PCR was performed using 20 pmol each of unlabeled hKPM8 and hKPM9, 1 pmol of end-labeled hKPM9, 0.2 mM dNTP, 2.5 µl of 10×PCR buffer, 2.5 U of Taq DNA polymerase and 1 µl of the first round PCR product from the ASA. Samples were amplified for 30 cycles, each consisting of 1 min at 94° C., 1 min at 50° C. and 1 min at 72° C. The PCR products were mixed with 12.5 µl of stop solution and denatured at 95° C. for 5 min. Samples of 1 µl each were loaded onto 8% sequencing gels and electrophoresed at 2000 V (approximately 50 V/cm) for 2.5 hours at room temperature. A sequence reaction of a known gene was used as a size marker in the electrophoresis on the polyacrylamide gel. The gel was dried on filter paper and exposed to Kodak X-Omat AR film at −80° C. for 5 hours.

Plasmid constructions. Human genomic DNA (25 ng) of the individuals with the different alleles was used as template to amplify promoter sequences spanning nucleotides −940 to +10 from the transcription initiation site of the human tissue kallikrein gene. The PCR was performed with the upstream primer hKPM1 and the downstream primer hKPM15 (5'-TGGAGGAACTGGGGAAC-3') (SEQ ID NO:13). The PCR products were gel-purified, filled-in with Klenow fragment of DNA polymerase I (BRL) and phosphorylated with T4 kinase (BRL). These DNA fragments were cloned into the XhoI site of the vector pGL2-Basic (Promega) which carries the luciferase structural gene. The fidelity of all constructs and insert orientation were determined by restriction enzyme mapping and nucleotide sequencing. The plasmid pCH110, which contains a functional LacZ gene under the direction of the SV40 early promoter, was purchased from Pharmacia. The plasmids used in the transfection studies were prepared with a DNA purification kit (Qiagen).

Cell culture. The human embryonic kidney cell line 293 (ATCC CRL 1573) was maintained in Dulbecco's modified Eagle's medium (D-MEM) (BRL) supplemented with 10% fetal calf serum. These cells were passaged 1:10 weekly at 37° C. in a 5% $CO_2$ incubator.

Transient transfection assays. Human 293 cells were co-transfected with 20 µg of hKLK1 promoter-luciferase reporter gene plasmids and 10 µg of plasmid pCH110. Electroporation was carried out with $6 \times 10^6$ cells in 200 µl of D-MEM medium using 0.2-cm gap cuvettes and an electrocell manipulator-600 (BTX). One shock was administered at 125 V and a capacitance of 800 microfarads. The cells were transferred to 6-well plates following the electroporation and the medium was changed in 24 hours. The cells were harvested 48 hours after replacement with fresh medium.

Luciferase and β-galactosidase assays. The cells were lysed in 110 µl of 1×Reporter Lysis Buffer (Promega) by incubation at room temperature for 15 minutes. Luciferase activity was assessed using the Promega Luciferase Assay System and a scintillation counter following the protocol recommended by the manufacturer. To correct for variations in transfection efficiency, β-galactosidase activity was determined. Briefly, 30 µl of cell extract was added to 30 µl of assay buffer containing 1.33 mg/ml o-nitrophenyl-β-D-galactopyranoside, 2 mM $MgCl_2$, 100 mM β-mercaptoethanol, 120 mM $Na_2HPO_4$ and 80 mM $NaH_2PO_4$ (pH 7.3). The reactions were incubated at 37° C. for up to 3 hours and terminated by the addition of 100 µl of 1 M $Na_2CO_3$. The optical density of the reaction was read at 420 nm with a spectrophotometer. The normalized luciferase/β-galactosidase activity for each plasmid was expressed as a percent of the activity recorded for the −940/+10 type B construct.

Statistical analysis. Allelic frequencies were calculated from the observed numbers of each allele and the total numbers of chromosomes examined. Based on the allelic frequencies, the observed genotypic distributions in this polymorphic region were tested to determine if they conform to Hardy-Weinberg equilibrium expectations based on the method described by Khoury et al. (1993). In the promoter analysis, the data for each construct were expressed as mean±SEM. Comparison of the promoter activities between various constructs was made by the Students' t-test. Differences were considered significant at a value of $P<0.05$.

Identification of polymorphism in the 5' flanking region of human tissue kallikrein gene. The 5' flanking region of the human tissue kallikrein gene was searched for polymorphisms in 108 unrelated subjects, consisting of 57 Caucasians, 33 African-Americans and 18 Asians. A genomic fragment of this region between +58 bp and −940 bp, was amplified by PCR and subjected to direct DNA sequencing. The fidelity of PCR amplification was ensured by sequencing two batches of the PCR products. Extensive variation was noticed in a GC-rich region located between −133 bp and −121 bp with respect to the transcription initiation site. Fifteen alleles were identified at this locus. These alleles vary in length from 12 bp to 17 bp and/or in nucleotide sequence by single-base transversion (Table 1). The greatest variability was found in the African-American population in which all of the alleles were detected. Six alleles (A, B, E, H, I and K) were observed in Caucasian subjects, including four length variations. Four alleles (A, B, H and K) were found in Asians.

Allelic frequency distribution and Test of Hardy-Weinberg Equilibrium. Table 2 summarizes the genotype frequencies of alleles in Caucasians, African-Americans and Asians. Alleles A and B have the highest prevalence in these subjects. Alleles H and K are also present with high frequencies in these three ethnic populations. These results show that the shared alleles between the three populations are the most frequent ones. Table 3 summarizes the observed and expected numbers of heterozygotes and homozygotes for each population. The calculation is based on the observed allelic frequencies. The results show that the polymorphisms exhibit Hardy-Weinberg equilibrium in the samples examined.

SSCP analysis. SSCP analysis was performed to determine its efficiency in identifying the alleles in this polymorphic region. Primer hKPM6 was labeled at the 5'-end and included in PCR amplification of a 180 bp fragment that encompassed the polymorphic region. The products were denatured and analyzed on non-denaturing polyacrylamide gels. Eleven samples, including 10 alleles in the form of either homozygotes or heterozygotes, were subjected to SSCP analysis. The SSCP band patterns were found to be reproducible under identical experimental conditions. Although the band mobilities were quite different between some genotypes such as AK heterozygote and II homozygote, other genotypes showed the same or very similar band mobilities in SSCP, such as BB and DD. Therefore, SSCP confirmed the existence of polymorphisms in this region, but does not appear to be suitable for genotyping of this polymorphic region due to the potential ambiguities.

Allele-specific amplification. ASA is a general method which can be optimized to detect all possible single-base mutations. In this polymorphic region, alleles A and B have the highest frequencies in all populations examined. They have a single-base difference in nucleotide sequence at position −128. It would be useful if these alleles could be rapidly genotyped. Two allele-specific upstream primers (hKPMA and hKPMB), differing in their 3' terminal nucleotide, were designed for alleles A and B. Both alleles accepted the same downstream primer for PCR. The PCR conditions were optimized to ensure that the mismatched primer would not function as the perfectly matched primer. A nested PCR protocol generated a 116 bp fragment. Each sample was examined using the two different primer sets in parallel and the results were consistent with those obtained by direct DNA sequencing.

Direct PCR analysis. This method was designed to facilitate the rapid assignment of alleles in genetic linkage analysis. Allele length can be precisely resolved to a single base by analysis of PCR products in polyacrylamide sequencing gels. The primers were designed for the nested PCR protocol in which a fragment of about 105 bp was finally generated. With a known sequence reaction ladder as the size marker, the sizes of the amplified fragments were determined accurately. The results were confirmed by DNA sequencing.

Figure 1:
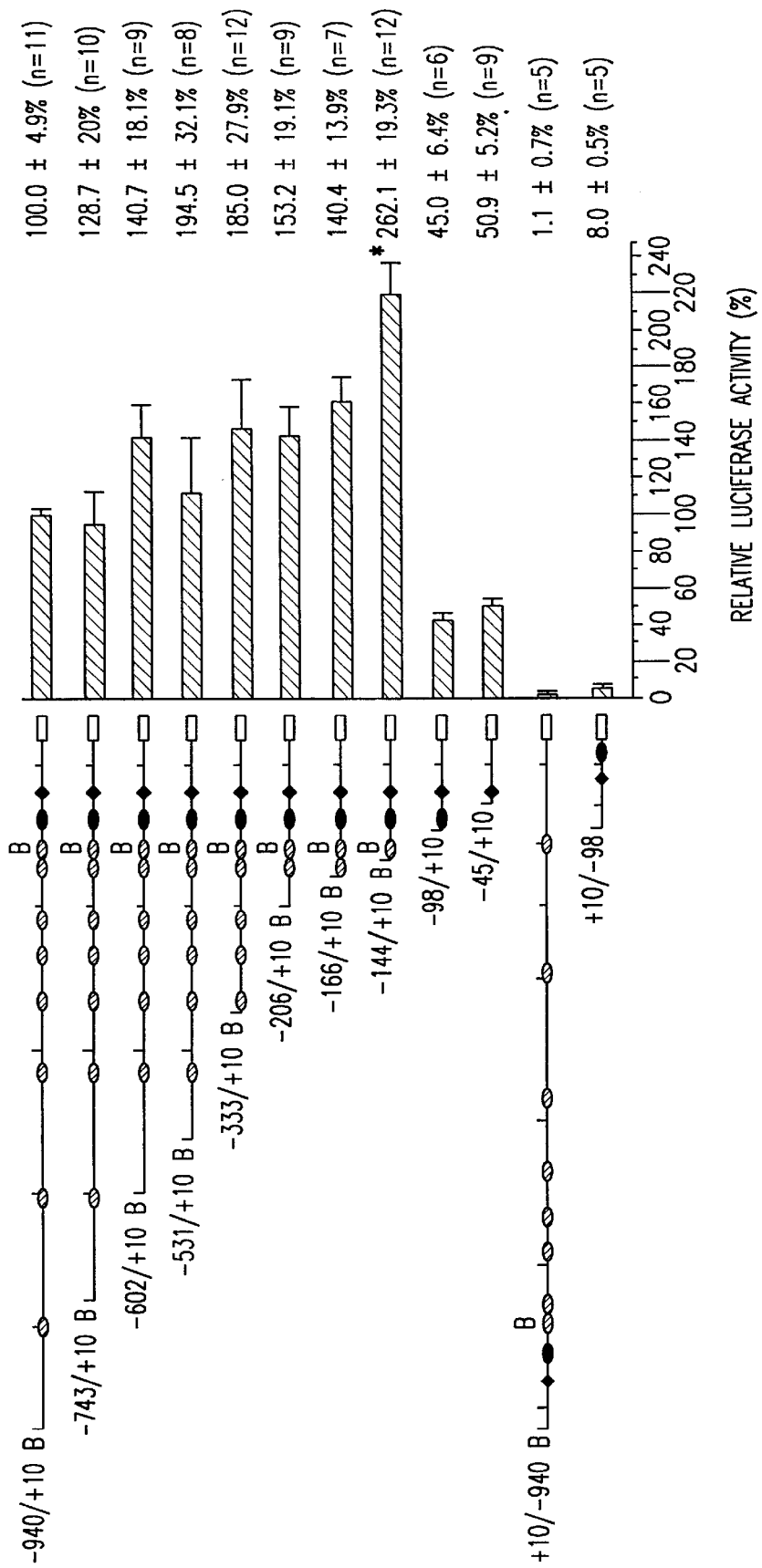
FIG. 1. Deletion analysis of the human tissue kallikrein gene promoter. The fusion constructs containing sequential 5'-deletions of allele B and luciferase reporter gene (Luc, open box) are shown schematically. The 5' endpoint of each construct is indicated at the left. Some putative response elements in this region are also shown. The transient transfection assay was done in human embryonic kidney 293 cells. The normalized relative luciferase activity (luciferase/β-galactosidase units) is calculated by comparison of the luciferase activity with that of the −940/+10 allele B construct as the reference (100%). Mean±SEM (n=5 to 12) is shown at right, the number of independent experiments used to calculate these data for each construct is shown in parentheses. "*", $P<0.05$.

Deletion analysis of the human tissue kallikrein gene promoter. To determine the sequence requirements for the human tissue kallikrein gene promoter and the contribution of the polymorphic region to its transcriptional activity, a series of deletion constructs were created with 5' variable ends and a common 3' end at residue +10. The ability of the respective fragments to direct transcription of the luciferase reporter gene was analyzed by transient transfection assay in human embryonic kidney 293 cells. The construct pSV-β-galactoside (pCH110) was co-transfected with the luciferase reporter constructs to provide an internal control for transfection efficiency in each experiment. The resulting luciferase activity was normalized with β-galactosidase activity. The normalized luciferase activities observed with difference deletions were compared to that of the −940/+10 (B) construct. Deletion of about 80% of the 5' flanking sequence (from −940 to −166) had little effect on the promoter activity (FIG. 1). Further deletion to −98 caused a dramatic reduction of promoter activity by more than five-fold. The control constructs with the promoter sequence in the anti-sense orientation showed very low promoter activities. These results indicate that the regulatory elements are present within the −166/−144 and −144/−98 regions, which are important as basal tissue kallikrein gene promoters. The region −166/−144 contributes to repression while the region −144/−98 contributes to stimulation of promoter activity. These results indicate a functional role for the polymorphic region in regulating transcriptional activity.

Figure 2:
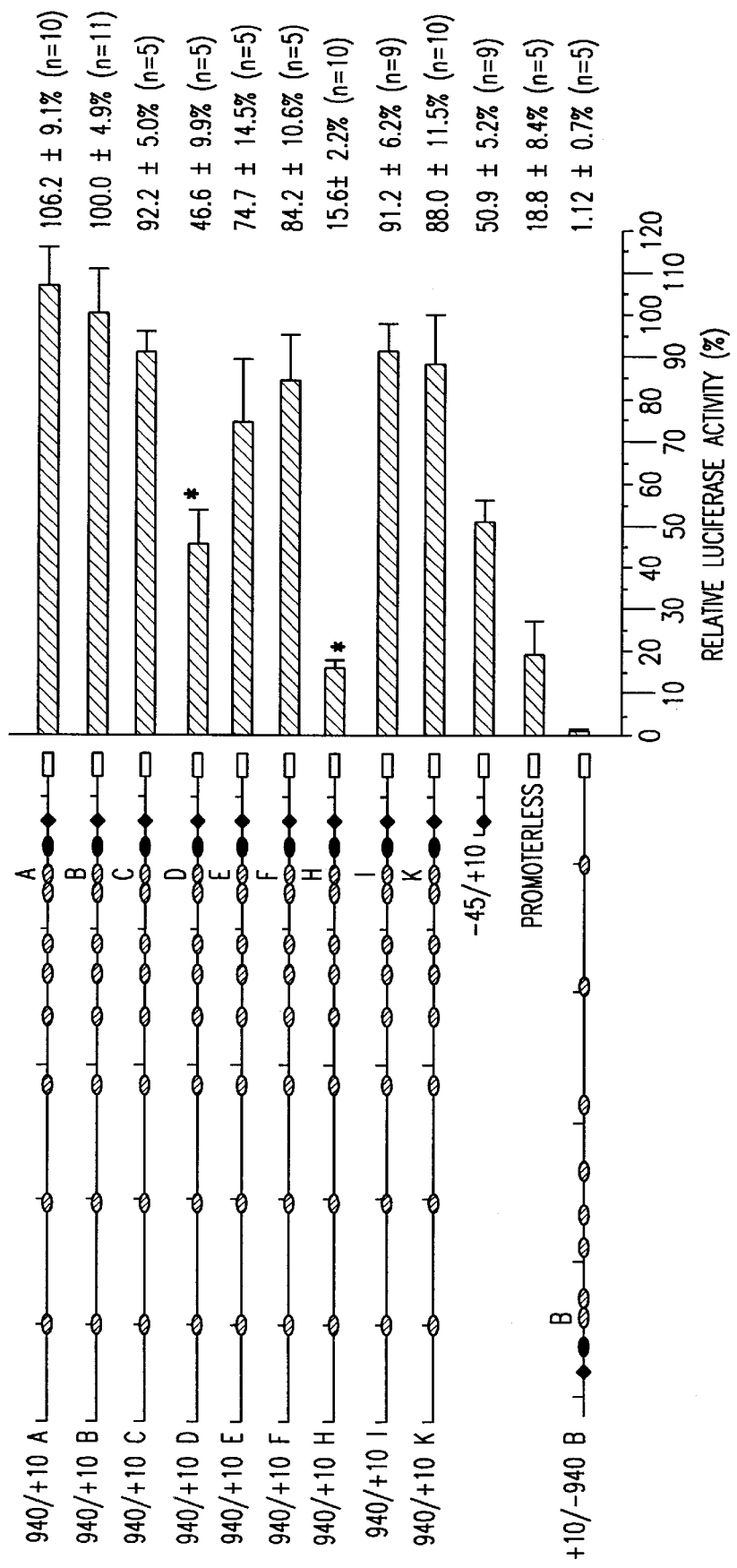
FIG. 2. Promoter activities of various alleles in the polymorphic region of the human tissue kallikrein gene. The −940/+10 deletion constructs containing various alleles and luciferase reporter gene are shown schematically. The transient transfection assay was done in human embryonic kidney 293 cells. The normalized relative luciferase activity (luciferase/β-galactosidase units) is calculated by comparison of the luciferase activity with that of the −940/+10 allele B construct as the reference (100%). Mean±SEM (n=5 to 10) is shown at right, the number of independent experiments used to calculate these data for each construct is shown in parentheses. "*", $P<0.05$.
Figure 3:
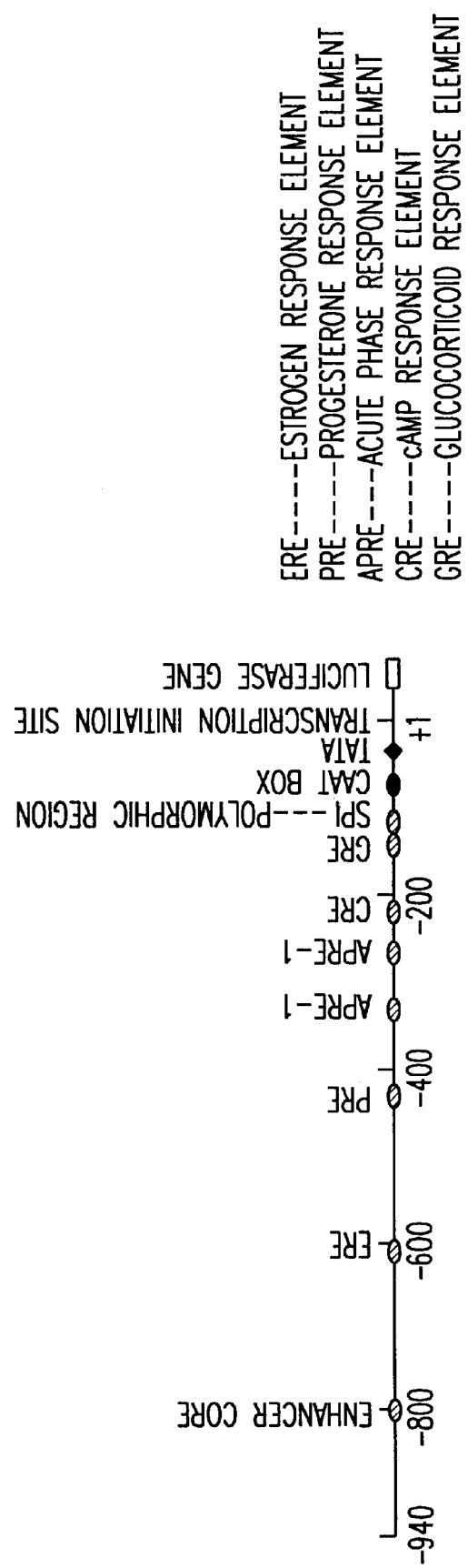
FIG. 3. Legend for identifying elements of the constructs shown in FIGS. 1 and 2.

Promoter activity analysis of various alleles. To determine the effect of this polymorphism on the transcriptional activity of the human tissue kallikrein gene promoter, nine −940/+10 deletion constructs, each containing one allele, were created. Transient transfection assays were conducted to test the promoter activity of each allelic variant Their promoter activities were tested in human 293 (embryonic kidney) cells (ATCC accession No. CRL 1573). Allele H exhibited only 10–20% promoter activity compared with other alleles and allele D showed less than 50% promoter activity (FIG. 2). The other alleles have similar promoter activities. The plasmid −940/+10 allele B in the antisense orientation and pGL2-Basic were also tested in this cell line as the controls. In these controls, the vector pGL2-Basic had 19% promoter activity and the construct +10/−940 B had only 1% activity.

Assay for correlating human tissue kallikrein promoter polymorphisms with increased or reduced risk of developing essential hypertension. This large scale study consists of collecting urine and DNA samples for 332 individuals belonging to 60 families. Blood pressure data are also collected for each individual. Urine tissue kallikrein levels are quantified according to standard protocols known in the art. The promoter region of the individual's's tissue kallikrein gene will be sequenced to identify the particular polymorphism (allele) in this region. A correlation will be made regarding an individual's genotype, urinary tissue kallikrein level and blood pressure, as analyzed using a two-tailed t test. The correlation can be extended further to include measurement of the amount of promoter activity demonstrated by a particular allele according to the molecular biology protocols described herein.

Because applicants show that the allele in the tissue kallikrein gene promoter is correlated with blood pressure status, direct analysis and comparison of an individual's genotype and phenotype can be used to identify alleles correlated with increased or decreased risk of developing essential hypertension. As a result of this correlation, it will be possible to predict an individual's risk of developing essential hypertension (phenotype) on the basis of the individual's genotype or amount of tissue kallikrein promoter activity, allowing for early intervention in individuals determined to be at risk and the prevention of the onset of essential hypertension and subsequent organ damage.

Results of statistical analysis. A total of 307 human subjects were genotyped according to the methods set forth herein. Specifically, the nucleic acid sequence of nucleotides −166 through −98 of the tissue kallikrein gene of each subject was determined and the subject's allelic genotype was identified according to the methods set forth in the Examples provided herein. Of these 307 subjects, 199 (65%) were identified as normotensive and 108 (35%) were identified as hypertensive on the basis of having a systolic/diastolic blood pressure of 140/90 mmHg or higher, according to methods set forth herein.

A statistical analysis using the chi square test was then conducted to identify a correlation between kallikrein allelic genotype and blood pressure distribution on the basis that the ratio of 65% normotensives versus 35% hypertensives is considered to be the normal distribution of blood pressure in this population. Kallikrein promoter alleles that are associated with a significant deviation from the normal blood pressure distribution (65% vs. 35%) are identified as having predictive value. The results of the statistical analysis are as follows:

a) 153 subjects have allele A. 101 subjects are normotensive (66%) and 52 subjects are hypertensive (34%). Allele A is identified as neutral because it does not alter the normal 65% vs 35% ratio. Allele A is dominant because a heterozygote with one A allele is the same as a homozygote in blood pressure phenotype.

b) 83 subjects have allele B. 56 subjects are normotensive (67%) and 27 subjects are hypertensive (33%). Allele B is identified as neutral because it does not alter the normal 65% vs 35% ratio. Allele B is dominant because a heterozygote with one B allele is the same as a homozygote in blood pressure phenotype.

c) 76 subjects are allele K. 55 subjects are normotensive (72%) and 21 subjects are hypertensive (28%). Allele K is identified as more frequently associated with normotensive phenotype.

d) 15 subjects have allele D. 6 subjects are normotensive (40%) and 9 subjects are hypertensive (60%). Allele D is identified as more frequently associated with hypertensive phenotype.

e) 35 subjects have allele H. 17 subjects are normotensive (49%) and 18 subjects are hypertensive (51%). Allele H is identified as more frequently associated with hypertensive phenotype.

The results of this analysis demonstrate that the D and H alleles of the promoter region of the human tissue kallikrein gene are correlated with an increased risk of developing essential hypertension and that subjects having these alleles have increased risk of developing hypertension. This risk increases from 35% to 51% for allele H and from 35% to 60% for allele D. These data also show that subjects having the A or B allele have the same risk of developing hypertension as that of the general population and that the K allele is correlated with a slightly reduced risk of developing hypertension, from 35% to 28%.

Correlation of human tissue kallikrein promoter polymorphisms with increased or reduced likelihood of regulating blood pressure with dietary salt intake, diuretics or angiotensin-converting enzyme inhibitors. A total of 262 subjects were recruited for this study (54% men and 46% women; 75% Caucasians and 25% African-Americans; 69% hypertensive and 31% normotensive; 18 to 66 years old; mean age=46.9±9.4). Antihypertensive medications, if used, were discontinued at least 2 weeks before the study. ACE inhibitors were discontinued 3 months before the study. Subjects with secondary hypertension were excluded. Blood pressure was measured three times in the left arm of seated subjects with a mercury column sphygmomanometer (>5 min apart), and the mean of three measurements was used. Data were collected on clinical variables including age, gender, race, cigarette smoking, alcohol assumption and medical history. All human studies were reviewed by the appropriate ethics committee and were performed in accordance with the ethical standards laid down in an appropriate version of the 1964 Declaration of Helsinki. All persons gave their informed consent prior to their inclusion in the study.

Genomic DNA was prepared from peripheral blood leukocytes as previously described (Bell et al. 1981). PCR was carried out in a 50 µl reaction volume containing 10 ng genomic DNA, 10 mM Tris-HCl (pH 8.3), 50 mM KCl, 1 mM $MgCl_2$, 200 µM dNTP, 1 µM hKPM6 (5'-GAATGCGTCCAGCGTGATCC-3') (SEQ ID NO:29) and hKPM7 (5'-AGCCCTTATCCCCTCAGAGC-3') (SEQ ID NO:30), and 2.5 U of Taq DNA polymerase. Thirty cycles of PCR were performed in a thermal cycler with a denaturing phase of 1 min at 94° C., annealing phase of 2 min at 60° C., and extension phase of 3 min at 72° C. PCR product of 2 µl was subjected to DNA sequence analysis (BRL sequencing system) using an internal primer hKPM8 (5'-GTGATCCAGGGCCTGCA-3') (SEQ ID NO 31). PCR and genotype analyses were processed in duplicate to eliminate possible errors that might be generated during PCR amplification.

The SAS system (Release 11, SAS Institute Inc, Cary, N.C.) was used to performed statistical analyses with adjustment for age, gender and race, using the procedures REG and LOGISTIC. All statistical tests were two sided, and a value of P<0.05 was considered statistically significant. The procedure of analysis of covariance of SAS was performed to measure how much variation can be accounted for by independent variables of age, gender, race and kallikrein genotype. Additive model was tested by comparing the overall contribution (24.5%) and the sum (25.1%) of contributions from the variables of age, gender, race and kallikrein genotype.

On admission to the metabolic ward, each subject was placed on a constant isocaloric diet of 10 mmol sodium and 100 mmol potassium, with 2000 ml water per day for 3 months. Some individuals began their low sodium diet as outpatients. 24-hour urine was collected from the participants and blood pressure was recorded. After 3 months on dietary salt restriction, reduction of systolic and diastolic blood pressure (BP) was observed among the majority of the participants, with the minority showing either no BP change or an increase (FIG. 8A & 8B). The BP reduction occurred in both hypertensive and normotensive individuals, regardless of their initial BP. These results show that while the majority of the participants could benefit from dietary salt restriction, a significant number of the participants derived no benefits or showed a negative effect upon salt restriction.

A comparison was also made with urinary kallikrein excretion and kallikrein genotypes. Genotypes with identical length polymorphisms were combined because of the small number of individuals in certain genotypic groups. The results (FIG. 4) show that most individuals (with polymorphism lengths of 16/15, 16/14 and 15/14) increased their urinary kallikrein excretion significantly upon salt restriction, while individuals with polymorphism length 14/14 (except BB genotype) showed no change. Individuals with BB genotype excreted more kallikrein on a high salt diet.

The relationship between the kallikrein genotype and BP response to sodium restriction was analyzed using a SAS statistical package with adjustment by race, gender and age. The results show that dietary sodium restriction induced a mean of 10 to 12% BP reduction among most of the subjects including those with kallikrein genotypes AA, BB and BK. Conversely, it induced only 2–4% BP reduction among those individuals with the specific genotype AK (FIGS. 6 & 7). These data indicate a genetic basis for urinary kallikrein levels and BP response to salt restriction. Both responses are heterogeneous at the population level but are primarily determined by the kallikrein genotypes at an individual level.

The influence of kallikrein genotype on the variance of BP responses to dietary sodium restriction was also quantified. The analysis of covariance by SAS estimated that the kallikrein genotype, gender and age accounted for approximately 10.9%, 8.99% and 5.19% to the variance of BP responses, respectively. Ethnicity weighed less than 0.001%, implying that genotypic difference in kallikrein could explain entirely the ethnic difference of hypertension among these subjects. This analysis also confirmed the additive model for the effects of age, gender, ethnicity and kallikrein genotype. The divergent allelic frequencies of the kallikrein promoter polymorphism between African-Americans and Caucasians have been reported previously (Song et al., 1997). It is not known if African-Americans share their kallikrein promoter alleles with West-Africans or if they have a unique allelic frequency. To address this issue, kallikrein genotypes were determined for 192 West-Africans, 378 Caucasians, and 215 African-Americans. Analysis of these data revealed that African-Americans do not possess any unique common alleles that are not found in West Africans. However, African-Americans and West-Africans do not share the same pattern of kallikrein promoter allele distribution (Table 4). For instance, the African-American population had significantly less occurrence of allele B than Caucasians but more occurrence of this allele than the West African group, whereas the situation for allele K was just the opposite (Table 4). Therefore, on the basis of the kallikrein genotype, African-Americans represent a special ethnic population genetically different from both Caucasians and West-Africans.

To explore the physiological mechanisms underlying the kallikrein genotype and salt sensitivity, the relationships between the kallikrein genotype and urine volume, urinary sodium and potassium excretion were analyzed. A significant association between kallikrein genotype and urine volume (FIG. 5) was observed. However, no correlation between the kallikrein genotype and urinary sodium and potassium excretion was detected. Under a high sodium diet, the kallikrein genotype BB was statistically associated with higher 24 hour-urine volume (FIG. 5). This difference was absent under a low sodium diet (FIG. 5). Consistently, allele B was consistently found to be linked to a high level of urinary kallikrein excretion under the high sodium diet, whereas the linkage was absent under the low sodium diet.

These data also have pharmacogenomic applications. For example, African-American hypertensive patients are known to respond to diuretics better than beta blockers and ACE inhibitors (Jamerson and DeQuattro 1996; Seedat 1999; Flack 1998). The reason for this was not previously known but can now be explained based on the data set forth herein which demonstrate that African-Americans have less allele B or "high kallikrein and diuretic" allele than Caucasians and thus are more likely to benefit from diuretics as opposed to other treatments for high blood pressure. Conversely, the data herein also indicate that individuals with B allele would more likely benefit from ACE inhibitors because kinin accumulation would be more pronounced in individuals with B or "high kallikrein and diuretic" allele. Collectively, these data provide a rational approach to drug selection based on kallikrein genotyping results.

Although the present process has been described with reference to specific details of certain embodiments thereof, it is not intended that such details should be regarded as limitations upon the scope of the invention except as and to the extent that they are included in the accompanying claims.

Throughout this application, various publications are referenced. The disclosures of these publications in their entireties are hereby incorporated by reference into this application in order to more fully describe the state of the art to which this invention pertains.

References

Ader, J. L., T. Tran-Van and F. Praddaude. Low urinary excretion of active and total kallikrein in young spontaneously hypertensive rats and effect of long-term angiotensin converting enzyme inhibition. *J. Hypertens.* 4: 151–153, 1986.

Ader J. L., T. Tran-Van and F. Praddaude. Renal tissue kallikrein in newborn and young SHR. *Am. J. Hypertens.* 1: 53S–55S, 1987.

Angotti E., E. Mele, F. Costanzo and E. V. Avvedimento. A polymorphism (G→A transition) in the −78 position of the apolipoprotein A-I promoter increases transcription efficiency. *J. Boil Chem.* 269: 17371–17374, 1994.

Bell G. I., J. H. Karam and W. J. Rutter. Polymorphic DNA region adjacent to the 5' end of the human insulin gene. *Proc. Natl. Acad. Sci. USA* 78: 5759–5763, 1981.

Berge K. E. and K. Berg. No effect of TaqI polymorphism at the human renal kallikrein (KLK1) locus on normal blood pressure level or variability. *Clin. Genet.* 44: 196–202, 1993.

Berge K. E. and K. Berg. A TaqI RFLP at the human renal kallikrein (KLK1) locus. *Clin. Genet.* 40: 256, 1991.

Berry T. D., S. J. Hasstedt, S. C. Hunt, L. L. Wu, J. B. Smith, O. Ash, H. Kuida and R. R. Williams. A gene for high urinary kallikrein may protect against hypertension in Utah kindreds. *Hypertension* 13: 3–8, 1989.

Brown C. J., K. A. Baltz and H. J. Edenberg. Expression of the human ADH2 gene: an unusual Sp 1-binding site in the promoter of a gene expressed at high levels in liver. *Gene* 121: 313–320, 1992.

Carretero O. A. and A. G. Scicli. The renal kallikrein-kinin system in human and experimental essential hypertension. *Clin. Wochenschr.* 56: 113–125, 1971.

Carretero O. A., C. Polomski, A. Hampton and A. G. Scicli. Urinary kallikrein, plasma renin and aldosterone in New Zealand genetically hypertensive (GH) rats. *Clin. Exp. Pharmacol. Physiol.* 3: 55–59, 1976.

Carretero O. A., V. M. Amin, T. Ocholik, A. G. Scicli and J. Koch. Urinary kallikrein in rats bred for their susceptibility and resistance to the hypertensive effect of salt. *Circ. Res.* 42: 727–731, 1978.

Cotton R. G. Current methods of mutation detection. *Mutat. Res.* 285: 125–144, 1993.

Dawson S. J., B. Wiman, A. Hamsten, F. Green, S. Humphries and A. M. Henney. The two allele sequences of a common polymorphism in the promoter of the plasminogen activator inhibitor-1 (PAI-1) gene respond differently to interleukin-1 in HepG2 cells. *J. Biol. Chem.* 268: 10739–10745, 1993.

Elliot R. and F. R. Nuzum. Urinary excretion of a depressor substance (kallikrein of Frey and Kraut) in arterial hypertension. *Endocrinology* 18: 462–474, 1934.

Evans B. A., Z. X. Yun, J. A. Close, G. W. Tregear, N. Kitamura, S. Nakanishi, D. F. Callen, E. Baker, V. J. Hyland, G. R. Sutherland and R. I. Richards. Structure and chromosomal localization of the human renal kallikrein gene. *Biochemistry* 27: 3124–3129, 1988.

Flack JM. Therapy of hypertension. In: Greenberg A, Cheung AK, Coffmann TM, Falk RJ, Jennette JC, editors. *Primer on Kidney Diseases.* Toronto: Academic Press, pp. 506–516, 1998.

Jamerson K and DeQuattro V. The impact of ethnicity on response to antihypertensive therapy. *Am. J. Med.* 101 (Suppl 3A):22s–32s, 1996.

Khoury M. J., Beaty T. E. and Cohen B. E. in *Fundamentals of Genetic Epidemiology.* Eds, Kelsey J., Marmot M. G., Stolley P. D., Vessey M. P. New York, Oxford University Press. Inc., p. 49–53, 1993.

MacMahon S, Peto R, Cutler J, Collins R, Sorlie P, Neaton J, Abbott R, Godwin J, Dyer A, and Stamler J. Blood pressure, stroke, and coronary heart disease. Part 1, Prolonged differences in blood pressure: prospective observational studies corrected for the regression dilution bias. *Lancet* 335: 765–774, 1990.

Margolius H. S., D. Horwitz, J. J. Pisano and H. R. Keiser. Urinary kallikrein in hypertension: relationship to sodium intake and sodium-retaining steroid. *Circ. Res.* 35: 820–825, 1974.

Margolius H. S., R. G. Geller, J. J. Pisano and A. Sjoerdsma. Altered urinary kallikrein excretion in human hypertension. *Lancet* 2: 1063–1065, 1971.

Newton C. R., A. Graham, L. E. Heptinstall, S. J. Powell, C. Summers, N. Kalsheker, J. C. Smith and A. F. Markham. Analysis of any point mutation in DNA. The amplification refractory mutation system (ARMS). *Nucleic Acids Res.* 17: 2503–2516, 1989.

Nichols W. C., J. J. Liepnieks, V. A. McKusick and M. D. Benson. Direct sequencing of the gene for Maryland/German familial amyloidotic polyneuropathy type II and genotyping by allele-specific enzymatic amplification. *Genomics* 5: 535–540, 1989.

Okayama H., D. T. Curiel, M. L. Brantly, M. D. Holmes and R. G. Crystal. Rapid, nonradioactive detection of mutations in the human genome by allele-specific amplification. *J. Lab. Clin. Med.* 114: 105–113, 1989.

Orita M., Y. Suzuki, T. Sekiya and K. Hayashi. Rapid and sensitive detection of point mutations and DNA polymorphisms using the polymerase chain reaction. *Genomics* 5: 874–879, 1989.

Pecker MS, and Laragh JH. Dietary salt and blood pressure: A perspective. *Hypertension* 17 (Suppl I): I97–I99, 1991.

Richards R. I., K. Holman, Y. Shen, H. Kozman, H. Harley, D. Brook and D. Shaw. Human glandular kallikrein genes: genetic and physical mapping of the KLK1 locus using a highly polymorphic microsatellite PCR marker. *Genomics* 11: 77–82, 1991.

Sambrook et al. *Molecular Cloning: A Laboratory Manual*, 2nd Ed., Cold Spring Harbor Laboratory, Cold Spring Harbor, N.Y., 1989.

Seedat YK. Hypertension in black South Africans. *J. Human Hypertension* 13:97–103, 1999.

Sarkar G., H. S. Yoon and S. S. Sommer. Screening for mutations by RNA single-strand conformation polymorphism (rSSCP): comparison with DNA-SSCP. *Nucleic Acids Res.* 20: 871–878, 1992.

Shimamoto, K., H. S. Margolis, J. Chao and A. P. Kaplan. The measurement of immunoreactive glandular kallikrein in human serum and its clinical application. *J. Lab. Clin. Med.* 103:731–738, 1984.

Sommer S. S., J. D. Cassady, J. L. Sobell and C. D. Bottema. A novel method for detecting point mutations or polymorphisms and its application to population screening for carriers of phenylketonuria. *Mayo. Clin. Proc.* 64: 1361–1372, 1989.

Song Q, Chao J, and Chao L. DNA polymorphisms in the 5'-flanking region of the human tissue kallikrein gene. *Human Genet.* 99 (6):727–34, 1997.

Wang J., W. Xiong, Z. Yang, T. Davis, M. J. Dewey, J. Chao and L. Chao. Human tissue kallikrein induces hypotension in transgenic mice. *Hypertension* 23: 236–243, 1994.

Williams R. R., Hunt S. C., Hasstedt S. J., Wu L. L., Barlow G. K., Stults B. M., Ash K. O. and Kuida H. in *Early Pathogenesis of primary Hypertension: Biological Markers of Genetically Predisposed Hypertension*. Eds, Hofman A., Grobbee D. E., Schalekamp M. A. D. H. Amsterdam, Elsevier Science Publishing Co. Inc., p. 187–208, 1987.

Wu D. Y., L. Ugozzoli, B. K. Pal and R. B. Wallace. Allele-specific enzymatic amplification of beta-globin genomic DNA for diagnosis of sickle cell anemia. *Proc. Natl. Acad. Sci. U S A* 86: 2757–2760, 1989.

TABLE 1

DNA sequence of alleles in the polymorphic region of the human tissue kallikrein gene

| Alleles | Sequence | Length |
|---|---|---|
| A | (SEQ ID NO:14) 5'-GGAGGGGGGGGGGC-3' | 14 |
| B | (SEQ ID NO:15) 5'-GGAGGCGGGGGGGC-3' | 14 |
| C | (SEQ ID NO:16) 5'-GGGGGGGGGGGGGC-3' | 14 |
| D | (SEQ ID NO:17) 5'-GGGGCGGGGGGGGC-3' | 14 |
| E | (SEQ ID NO:18) 5'-GGAGGGCGGGGGGC-3' | 14 |

TABLE 1-continued

DNA sequence of alleles in the polymorphic region of the human tissue kallikrein gene

| Alleles | Sequence | Length |
|---|---|---|
| F | (SEQ ID NO:19) 5'-GGAGCGGGGGGGGGC-3' | 15 |
| G | (SEQ ID NO:24) 5'-GGAGCGGGGGGGC-3' | 14 |
| H | (SEQ ID NO:20) 5'-GGAGGGGGGGGGGGC-3' | 15 |
| I | (SEQ ID NO:21) 5'-GGAGGGGGGGGGC-3' | 13 |
| J | (SEQ ID NO:25) 5'-GGAGGGGGGGGC-3' | 12 |
| K | (SEQ ID NO:22) 5'-GGAGGGGGGGGGGGGGC-3' | 16 |
| M | (SEQ ID NO:26) 5'-GGAGGGGGGGGGGGGGGC-3' | 17 |
| P | (SEQ ID NO:23) 5'-GGAGGGCGGGGGC-3' | 13 |
| Q | (SEQ ID NO:28) 5'-GGGGGGGGGGGGC-3' | 13 |
| R | (SEQ ID NO:27) 5'-GGAGGGGGGGGGCGGC-3' | 16 |

TABLE 2

Allelic frequencies in the polymorphic region of the human tissue kallikrein gene

| | Alleles | | | | | |
|---|---|---|---|---|---|---|
| | Caucasians (57 subjects) | | African-Americans (33 subjects) | | Asians (18 subjects) | |
| | Numbers Observed | Allelic Frequency | Numbers Observed | Allelic Frequency | Numbers Observed | Allelic Frequency |
| A | 48 | 0.421 | 13 | 0.197 | 22 | .0611 |
| B | 33 | 0.290 | 12 | 0.182 | 4 | 0.111 |
| C | 0 | 0.000 | 4 | 0.061 | 0 | 0.000 |
| D | 0 | 0.000 | 4 | 0.061 | 0 | 0.000 |
| E | 1 | 0.009 | 4 | 0.061 | 0 | 0.000 |
| F | 0 | 0.000 | 1 | 0.015 | 0 | 0.000 |
| H | 16 | 0.140 | 6 | 0.091 | 9 | 0.250 |
| I | 2 | 0.018 | 12 | 0.182 | 0 | 0.000 |
| K | 14 | 0.123 | 9 | 0.136 | 1 | 0.028 |
| P | 0 | 0.000 | 1 | 0.015 | 0 | 0.000 |

TABLE 3

Observed and expected numbers of genotypes in the polymorphic region among different populations, assuming Hardy-Weinberg equilibrium

| | Caucasians (57 subjects) | | African-Americans (33 subjects) | | Asians (18 subjects) | |
|---|---|---|---|---|---|---|
| Genotypes | Observed Numbers | Expected Numbers | Observed Numbers | Expected Numbers | Observed Numbers | Expected Numbers |
| Homozygote | 12 | 16.90 | 6 | 4.73 | 7 | 8.08 |
| Heterozygote | 45 | 40.1 | 27 | 28.27 | 11 | 9.92 |
| $\chi^2$ | 2.0187 | | 0.3981 | | 0.2619 | |

TABLE 4 hKLKI Promoter Allele Distriction in three populations

| Alleles | Caucasians (n = 378) | African-Americans (n = 215) | West Africans (N = 192) |
|---|---|---|---|
| A | 0.356 | 0.284 | 0.286 |
| B | 0.282 | 0.112 | 0.052 |
| C | 0.000 | 0.067 | 0.073 |
| D | 0.001 | 0.051 | 0.016 |
| E | 0.016 | 0.021 | 0.060 |
| F | 0.000 | 0.019 | 0.008 |
| G | 0.011 | 0.047 | 0.016 |
| H | 0.188 | 0.199 | 0.094 |
| I | 0.042 | 0.140 | 0.190 |
| J | 0.000 | 0.009 | 0.005 |
| K | 0.091 | 0.128 | 0.185 |
| M | 0.011 | 0.002 | 0.003 |
| P | 0.001 | 0.002 | 0.003 |
| Q | 0.000 | 0.000 | 0.010 |
| R | 0.001 | 0.000 | 0.00 |

What is claimed is:

1. A method of identifying a human subject having an increased likelihood of regulating blood pressure with restricted dietary sodium intake, comprising determining in the subject the presence of an allele in the tissue kallikrein gene promoter region consisting of nucleotides at positions −166 through −98, wherein the allele is correlated with an increased likelihood of regulating blood pressure with restricted dietary sodium intake, thereby identifying the subject having an increased likelihood of regulating blood pressure with restricted dietary sodium intake.

2. A method of identifying a human subject having an increased likelihood of regulating blood pressure with restricted dietary sodium intake, comprising:
   a) correlating the presence of an allele in the tissue kallikrein gene promoter region consisting of nucleotides at positions −166 through −98 with an increased likelihood of regulating blood pressure with restricted dietary sodium intake; and
   b) detecting the allele of step a) in the subject, thereby identifying a subject having an increased likelihood of regulating blood pressure with restricted dietary sodium intake.

3. A method of identifying an allele in the tissue kallikrein gene promoter region consisting of nucleotides at positions −166 through −98 correlated with an increased likelihood of regulating blood pressure with restricted dietary sodium intake, comprising:
   a) determining in a subject the presence of an allele in the tissue kallikrein gene promoter region consisting of nucleotides at positions −166 through −98; and
   b) correlating the presence of the allele of step (a) with the ability of the subject to regulate blood pressure by restricted dietary sodium intake, thereby identifying an allele correlated with an increased likelihood of regulating blood pressure by restricted dietary sodium intake.

4. A method of identifying a human subject having a reduced likelihood of regulating blood pressure with restricted dietary sodium intake, comprising determining in the subject the presence of an allele in the tissue kallikrein gene promoter region consisting of nucleotides at positions −166 through −98, wherein the allele is correlated with a reduced likelihood of regulating blood pressure with restricted dietary sodium intake, thereby identifying the subject having a reduced likelihood of regulating blood pressure with restricted dietary sodium intake.

5. A method of identifying a human subject having a reduced likelihood of regulating blood pressure with restricted dietary sodium intake, comprising:
   a) correlating an allele in the tissue kallikrein gene promoter region consisting of nucleotides at positions −166 through −98 with a reduced likelihood of regulating blood pressure with restricted dietary sodium intake; and
   b) detecting the presence of the allele of step a) in the subject, thereby identifying a subject having a reduced likelihood of regulating blood pressure with restricted dietary sodium intake.

6. A method of identifying an allele in the tissue kallikrein gene promoter region consisting of nucleotides at positions −166 through −98 correlated with a reduced likelihood of regulating blood pressure with restricted dietary sodium intake, comprising:

a) determining in a subject the presence of an allele in the tissue kallikrein gene promoter region consisting of nucleotides at positions −166 through −98; and b) correlating the presence of the allele of step (a) with the inability of the subject to regulate blood pressure by restricted dietary sodium intake, thereby identifying the allele as correlated with a reduced likelihood of regulating blood pressure by restricted dietary sodium intake.

7. A method of identifying a subject at reduced risk of having essential hypertension, comprising determining in the subject the presence of an allele in the tissue kallikrein gene promoter region consisting of nucleotides at positions −166 through −98 correlated with a reduced risk of developing essential hypertension, thereby identifying the subject having a reduced risk of developing essential hypertension.

8. A method of identifying a human subject having a reduced risk of developing essential hypertension, comprising:

a) correlating the presence of a nucleic acid sequence at nucleotides −166 through −98 in a human tissue kallikrein gene with a reduced risk of developing essential hypertension; and b) determining the nucleic acid sequence of nucleotides −166 through −98 of the subject's tissue kallikrein gene, whereby a subject having a nucleic acid sequence at nucleotides −166 through −98 in the tissue kallikrein gene correlated with a reduced risk of developing essential hypertension is identified having a reduced risk of developing essential hypertension.

9. A method of identifying an allele in the promoter region of a human tissue kallikrein gene correlated with a reduced risk of developing essential hypertension, comprising:

a) determining the nucleic acid sequence of the nucleotides at positions −166 through −98 in the human tissue kallikrein gene from a subject; and b) correlating the presence of the nucleic acid sequence of the nucleotides at positions −166 through −98 in the human tissue kallikrein gene of the subject with the absence of essential hypertension in the subject, whereby the nucleic acid sequence of the nucleotides at positions −166 through −98 in the promoter region of the human tissue kallikrein gene identifies an allele correlated with a reduced risk of developing essential hypertension.

10. A method of identifying a human subject having an increased likelihood of regulating blood pressure with a diuretic, comprising determining in the subject the presence of an allele in the tissue kallikrein gene promoter region consisting of nucleotides at positions −166 through −98, wherein the allele is correlated with an increased likelihood of regulating blood pressure with a diuretic, thereby identifying the subject having an increased likelihood of regulating blood pressure with a diuretic.

11. A method of identifying a human subject having an increased likelihood of regulating blood pressure with a diuretic, comprising:

a) correlating the presence of an allele in the tissue kallikrein gene promoter region consisting of nucleotides at positions −166 through −98 with an increased likelihood of regulating blood pressure with a diuretic; and b) detecting the allele of step a) in the subject, thereby identifying a subject having an increased likelihood of regulating blood pressure with a diuretic.

12. A method of identifying an allele in the tissue kallikrein gene promoter region consisting of nucleotides at positions −166 through −98, correlated with an increased likelihood of regulating blood pressure with a diuretic, comprising:

a) determining in a subject the presence of an allele in the tissue kallikrein gene promoter region consisting of nucleotides at positions −166 through −98; and b) correlating the presence of the allele of step (a) with the ability of the subject to regulate blood pressure with a diuretic, thereby identifying an allele correlated with an increased likelihood of regulating blood pressure with a diuretic.

13. A method of identifying a human subject having a reduced likelihood of regulating blood pressure with a diuretic, comprising determining in the subject the presence of an allele in the tissue kallikrein gene promoter region consisting of nucleotides at positions −166 through −98, wherein the allele is correlated with a reduced likelihood of regulating blood pressure with a diuretic, thereby identifying the subject having a reduced likelihood of regulating blood pressure with a diuretic.

14. A method of identifying a human subject having a reduced likelihood of regulating blood pressure with a diuretic, comprising:

a) correlating an allele in the tissue kallikrein gene promoter region consisting of nucleotides at positions −166 through −98 with a reduced likelihood of regulating blood pressure with a diuretic; and b) detecting the allele of step a) in the subject, thereby identifying the subject having a reduced likelihood of regulating blood pressure with a diuretic.

15. A method of identifying an allele in the tissue kallikrein gene promoter region consisting of nucleotides at positions −166 through −98 correlated with a reduced likelihood of regulating blood pressure with a diuretic, comprising:

a) determining in the subject the presence of an allele in the tissue kallikrein gene promoter region consisting of nucleotides at positions −166 through −98; and b) correlating the presence of the allele of step (a) with the inability of the subject to regulate blood pressure with a diuretic, thereby identifying the allele as correlated with a reduced likelihood of regulating blood pressure with a diuretic.

16. A method of identifying a human subject having an increased likelihood of regulating blood pressure with an angiotensin-converting enzyme inhibitor, comprising determining in the subject the presence of an allele in the tissue kallikrein gene promoter region consisting of nucleotides at positions −166 through −98, wherein the allele is correlated with an increased likelihood of regulating blood pressure with an angiotensin-converting enzyme inhibitor, thereby identifying the subject having an increased likelihood of regulating blood pressure with an angiotensin-converting enzyme inhibitor.

17. A method of identifying a human subject having an increased likelihood of regulating blood pressure with an angiotensin-converting enzyme inhibitor, comprising:

a) correlating the presence of an allele in the tissue kallikrein gene promoter region consisting of nucleotides at positions −166 through −98 with an increased likelihood of regulating blood pressure with an angiotensin-converting enzyme inhibitor; and b) detecting the allele of step a) in the subject, thereby identifying the subject having an increased likelihood of regulating blood pressure with an angiotensin-converting enzyme inhibitor.

18. A method of identifying an allele in the tissue kallikrein gene promoter region consisting of nucleotides at positions −166 through −98 correlated with an increased likelihood of regulating blood pressure with an angiotensin-converting enzyme inhibitor, comprising:
   a) determining in the subject the presence of an allele in the tissue kallikrein gene promoter region consisting of nucleotides at positions −166 through −98; and
   b) correlating the presence of the allele of step (a) with the ability of the subject to regulate blood pressure with an angiotensin-converting enzyme inhibitor, thereby identifying an allele correlated with an increased likelihood of regulating blood pressure with an angiotensin-converting enzyme inhibitor.

19. A method of identifying a human subject having a reduced likelihood of regulating blood pressure with an angiotensin-converting enzyme inhibitor, comprising determining in the subject the presence of an allele in the tissue kallikrein gene promoter region consisting of nucleotides at positions −166 through −98, wherein the allele is correlated with a reduced likelihood of regulating blood pressure with an angiotensin-converting enzyme inhibitor, thereby identifying the subject having a reduced likelihood of regulating blood pressure with an angiotensin-converting enzyme inhibitor.

20. A method of identifying a human subject having a reduced likelihood of regulating blood pressure with an angiotensin-converting enzyme inhibitor, comprising:
   a) correlating an allele in the tissue kallikrein gene promoter region consisting of nucleotides at positions −166 through −98 with a reduced likelihood of regulating blood pressure with an angiotensin-converting enzyme inhibitor; and
   b) detecting the allele of step a) in the subject, thereby identifying the subject having a reduced likelihood of regulating blood pressure with an angiotensin-converting enzyme inhibitor.

21. A method of identifying an allele in a portion of the tissue kallikrein gene promoter region consisting of nucleotides at positions −166 through −98 correlated with a reduced likelihood of regulating blood pressure with an angiotensin-converting enzyme inhibitor, comprising:
   a) determining in the subject the presence of an allele in the tissue kallikrein gene promoter region consisting of nucleotides at positions −166 through −98; and
   b) correlating the presence of the allele of step (a) with the inability of the subject to regulate blood pressure with an angiotensin-converting enzyme inhibitor, thereby identifying the allele as correlated with a reduced likelihood of regulating blood pressure with an angiotensin-converting enzyme inhibitor.

22. An isolated nucleic acid consisting of the nucleotide sequence of SEQ ID NO:28 (allele Q).

* * * * *